United States Patent
Concha et al.

(10) Patent No.: US 11,254,718 B2
(45) Date of Patent: Feb. 22, 2022

(54) ALPHA-SYNUCLEIN SUBSTRATES AND METHODS FOR MAKING AND USING THE SAME

(71) Applicant: Amprion, Inc., San Francisco, CA (US)

(72) Inventors: Luis Concha, San Diego, CA (US);
Carly Farris, San Diego, CA (US);
Bret Holguin, San Diego, CA (US);
Yihua Ma, Corona, CA (US)

(73) Assignee: Amprion, Inc., San Francisco, CA (US)

( * ) Notice: Subject to any disclaimer, the term of this patent is extended or adjusted under 35 U.S.C. 154(b) by 0 days.

(21) Appl. No.: 17/323,919

(22) Filed: May 18, 2021

(65) Prior Publication Data

US 2021/0277076 A1 Sep. 9, 2021

Related U.S. Application Data

(63) Continuation-in-part of application No. 17/011,374, filed on Sep. 3, 2020, now Pat. No. 11,079,396.

(60) Provisional application No. 63/073,420, filed on Sep. 1, 2020, provisional application No. 63/073,424, filed on Sep. 1, 2020, provisional application No. 63/045,593, filed on Jun. 29, 2020, provisional application No. 63/042,679, filed on Jun. 23, 2020, provisional application No. 63/040,144, filed on Jun. 17, 2020, provisional application No. 63/026,394, filed on May 18, 2020, provisional application No. 62/895,535, filed on Sep. 4, 2019.

(51) Int. Cl.

| C12N 1/20 | (2006.01) |
| C07K 14/47 | (2006.01) |
| C12N 15/70 | (2006.01) |
| C07K 1/34 | (2006.01) |
| C12N 1/06 | (2006.01) |
| B01L 3/00 | (2006.01) |

(52) U.S. Cl.
CPC ............ C07K 14/47 (2013.01); B01L 3/5027 (2013.01); C07K 1/34 (2013.01); C12N 1/06 (2013.01); C12N 15/70 (2013.01)

(58) Field of Classification Search
CPC .................................. C12N 1/20; C12N 15/90
See application file for complete search history.

(56) References Cited

U.S. PATENT DOCUMENTS

2021/0063416 A1* 3/2021 Concha .............. G01N 33/6896

FOREIGN PATENT DOCUMENTS

| CN | 110551195 | 12/2019 |
| WO | 2012061788 | 5/2012 |

OTHER PUBLICATIONS

International Search Report and Written Opinion issued in PCT/US2021/033016, dated Nov. 3, 2021.

* cited by examiner

*Primary Examiner* — Tekchand Saidha
(74) *Attorney, Agent, or Firm* — Kern Kendrick, LLC; Benjamen E. Kern

(57) ABSTRACT

An expression vector is provided for production of human alpha-synuclein (αS) protein or a conservative variant thereof that exhibits a decreased tendency to self-aggregate in an αS seed amplification assay (SAA). The expression vector comprises a nucleic acid sequence coding for human αS protein or a conservative variant, the nucleic acid sequence comprising codons that have been optimized to produce human αS protein or a conservative variant when expressed by a host cell such as *E. coli*. The codons have been optimized to avoid amino acid misincorporation in the expressed protein. Methods for purification of the expressed protein are also provided.

13 Claims, 16 Drawing Sheets

Specification includes a Sequence Listing.

ALPHA-SYNUCLEIN SUBSTRATES AND METHODS FOR MAKING AND USING THE SAME

CROSS-REFERENCE TO RELATED APPLICATIONS

This application claims priority from U.S. Provisional Patent Application No. 63/026,394, filed on May 18, 2020. This application is also a continuation in part of U.S. Nonprovisional patent application Ser. No. 17/011,374, filed on Sep. 3, 2020, which claims priority from U.S. Provisional Patent Application No. 62/895,535, filed on Sep. 4, 2019; U.S. Provisional Patent Application No. 63/040,144, filed on Jun. 17, 2020; U.S. Provisional Patent Application No. 63/042,679, filed on Jun. 23, 2020; U.S. Provisional Patent Application No. 63/045,593, filed on Jun. 29, 2020; U.S. Provisional Patent Application No. 63/073,420, filed on Sep. 1, 2020; and U.S. Provisional Patent Application No. 63/073,424, filed on Sep. 1, 2020. Each of these Related Applications is incorporated by reference herein in its entirety.

SEQUENCE LISTING

A Sequence Listing has been submitted electronically in ASCII format and is hereby incorporated by reference in its entirety. The ASCII copy, created on May 18, 2021, is named Amprion-SUBS-AS-US_ST25.txt and is 39,802 bytes in size.

BACKGROUND

Certain degenerative brain diseases, collectively termed "synucleinopathies," involve pathological accumulation of misfolded alpha-synuclein ($\alpha$S) protein in the brain of affected subjects. A misfolded $\alpha$S protein is an $\alpha$S protein having a different structural conformation than it has when involved in its typical, nonpathogenic normal function within a biological system. A misfolded $\alpha$S protein may aggregate and may exist in or as an aggregate. A misfolded $\alpha$S protein may localize in an $\alpha$S protein aggregate. A misfolded $\alpha$S protein may be a non-functional protein. A misfolded $\alpha$S protein may be a pathogenic conformer of the $\alpha$S protein.

Synucleinopathies include Parkinson's disease (PD), dementia with Lewy bodies (DLB), and multiple system atrophy (MSA), as well as rare neuroaxonal dystrophies. Several lines of evidence indicate that the process of $\alpha$S misfolding and aggregation may begin years or decades before the onset of clinical symptoms and substantial brain damage. Thus, detection of $\alpha$S aggregates and/or misfolded $\alpha$S protein to facilitate early diagnosis of synucleinopathies could prove crucial to permit intervention before irreversible neuropathological changes occur.

Unfortunately, soluble, misfolded $\alpha$S protein is present in such low amounts in bodily fluids that it is very difficult to detect. Recently, however, significant advances have been made in the detection of misfolded $\alpha$S aggregates (i.e., non-covalent associations of misfolded $\alpha$S protein), particularly via Seed Amplification Assay (SAA) (formerly known as protein misfolding cyclic amplification (PMCA)). See, e.g., US20160077111A1, US20210063416A1, and U.S. Nonprovisional patent application Ser. No. 17/154,966, each of which is incorporated by reference herein in its entirety. Briefly, a biological sample (e.g., blood, skin, cerebrospinal fluid, or the like) is contacted with a pre-incubation mixture, the pre-incubation mixture comprising a monomeric $\alpha$S substrate; a buffer composition; a salt; and an indicator, to form an incubation mixture. Multiple incubation cycles are conducted on the incubation mixture. Each incubation cycle comprises: (1) incubating the incubation mixture effective to cause misfolding and/or aggregation of the monomeric $\alpha$S substrate in the presence of any soluble, misfolded $\alpha$S protein present in the biological sample, and (2) physically disrupting the incubation mixture to "de-aggregate," i.e., break up or disrupt, the misfolded $\alpha$S aggregates to release smaller aggregates. The $\alpha$S aggregates may then act as "seeds." Detection of misfolded $\alpha$S aggregate via indicator fluorescence indicates the presence of soluble, misfolded $\alpha$S protein in the biological sample. An example depiction of the $\alpha$S-SAA process with a biological sample containing soluble, misfolded $\alpha$S protein is shown in FIG. 1.

A significant limitation to $\alpha$S-SAA technology is the difficulty of producing SAA-competent monomeric $\alpha$S substrate at a sufficient scale for widespread testing. One approach to producing SAA-competent monomeric $\alpha$S substrate has been to transform into an enterobacterial host cell (e.g., *Escherichia coli* ("*E. coli*")) an expression vector comprising a nucleic acid sequence coding for human $\alpha$S protein, such as the plasmid represented by SEQ ID NO: 4; culture the enterobacterial host cell under conditions effective to produce the monomeric human $\alpha$S protein; obtain the human $\alpha$S protein from the enterobacterial host cell; and purify the human $\alpha$S protein to yield recombinant monomeric $\alpha$S substrate. However, the resultant monomeric $\alpha$S substrate has, in some instances, contained "misincorporated" cysteine in place of tyrosine, especially at position 136. "Misincorporation" refers to the process by which certain amino acids, e.g., cysteine, may be unintentionally substituted for other amino acids, e.g., tyrosine, when expressing a nucleic acid for a protein of one organism, e.g., a human nucleic acid encoding human $\alpha$S protein, in a host cell, e.g., a microorganism such as *E. coli*. The presence of cysteine residues in monomeric $\alpha$S substrate can lead to self-aggregation and misfolding by dimerization.

While aggregation of $\alpha$S protein is an expected part of the pathology of misfolded protein disorders and is used to advantage in $\alpha$S-SAA, it is crucial for monomeric $\alpha$S substrate to self-aggregate as little as possible. Self-aggregation refers to aggregation that would occur even in the absence of soluble, misfolded $\alpha$S protein in the biological sample. The propensity to self-aggregate is an intrinsic characteristic of $\alpha$S protein that resides in its amino acid sequence.

Depending on the relative kinetics and extent, self-aggregation and misfolding of the monomeric $\alpha$S substrate can prove to be a fatal factor in the use of $\alpha$S-SAA to amplify and detect misfolded $\alpha$S aggregate in a biological sample. When self-aggregation of the monomeric $\alpha$S substrate occurs, the result may be a "false positive"—that is, misfolded $\alpha$S aggregate is detected notwithstanding that no soluble, misfolded $\alpha$S protein was present in the biological sample—or an inaccurately high quantitative assessment of soluble, misfolded $\alpha$S protein in the biological sample.

Another limitation of existing monomeric $\alpha$S substrates is the failure of the monomeric $\alpha$S substrate to aggregate in the presence of soluble, misfolded $\alpha$S protein in the biological sample. This can occur, among other times, when the monomeric $\alpha$S substrate lacks sufficient homology with the soluble, misfolded $\alpha$S protein. When aggregation of the monomeric $\alpha$S substrate and soluble, misfolded $\alpha$S protein in the biological sample do not occur, the result may be a "false negative"—that is, misfolded $\alpha$S aggregate is not detected notwithstanding that soluble, misfolded αS protein was present in the biological sample—or an inaccurately low quantitative assessment of soluble, misfolded αS protein in the biological sample.

Thus, self-aggregation and misfolding of the monomeric αS substrate on the one hand, and a failure to aggregate with soluble, misfolded αS protein in the biological sample on the other, can result in misdiagnosis or inaccurate prognosis of tested subjects. Accordingly, there is a need for monomeric αS substrate that, together with proper SAA conditions, reduces, slows, or prevents self-aggregation when used in αS-SAA, yet retains its activity in the presence of soluble, misfolded αS protein in a biological sample.

SUMMARY

An expression vector is provided for production of human αS protein or a conservative variant thereof (ultimately "monomeric αS substrate") that exhibits a decreased tendency to self-aggregate in αS-SAA. The expression vector comprises a nucleic acid sequence coding for human αS protein or a conservative variant thereof, the nucleic acid sequence comprising codons that have been optimized to produce human αS protein or a conservative variant when expressed by an enterobacterial host cell such as *E. coli*. In some aspects, the codons have been optimized to avoid amino acid misincorporation. In some aspects, the codons have been optimized to avoid cysteine misincorporation in the expressed protein. In further aspects, the codons have been optimized to avoid cysteine misincorporation in at least one of positions 39, 125, 133, and 136 of the expressed protein.

In one aspect, the expression vector may comprise a coding nucleic acid sequence represented by SEQ ID NO: 1 or having at least 90% identity with SEQ ID NO: 1. In one aspect, the expression vector may be a plasmid. For example, the expression vector may be a plasmid that enables the expression of a protein by means of the T7-lac operon system. In one aspect, the expression vector may be a plasmid comprising SEQ ID NO: 1, as represented by SEQ ID NO: 2 or having at least 90% identity with SEQ ID NO: 2. In some aspects, the monomeric αS substrate is represented by SEQ ID NO: 6.

Also provided is a method for making a purified monomeric human αS substrate or a conservative variant. The method comprises transforming into a host cell an expression vector comprising a nucleic acid sequence coding for monomeric human αS protein or a conservative variant, the nucleic acid sequence comprising codons that have been optimized to avoid amino acid misincorporation in the expressed protein; culturing the host cell under conditions effective to produce the monomeric human αS protein or a conservative variant; obtaining the monomeric human αS protein or a conservative variant from the host cell; and purifying the monomeric human αS protein or a conservative variant by subjecting the human αS protein or a conservative variant to one or more acid precipitation steps at a pH of about 3.5 or less, followed by chromatography, to yield the purified monomeric human αS substrate or a conservative variant. In some aspects, the host cell is an enterobacteria such as *E. coli*, e.g., *E. coli* B121(DE3), BL21(DE3)-pLysS, and the like. In such aspects, the method further comprises eliminating bacterial lipids and/or adding lipopolysaccharide ("LPS") to the monomeric human αS substrate or a conservative variant after purification.

Finally, a recombinant enterobacterial cell is provided, the recombinant enterobacterial cell comprising an expression vector for production of human αS protein or a conservative variant, the expression vector comprising a nucleic acid sequence coding for human αS protein or a conservative variant, the nucleic acid sequence comprising codons that have been optimized to produce human αS protein or a conservative variant without amino acid misincorporation when expressed by the cell.

BRIEF DESCRIPTION OF THE FIGURES

The present invention may be more readily understood by reference to the following Figures, wherein:

FIG. 1 is an example depiction of the "fast" αS-SAA process using a biological sample that contains soluble, misfolded αS protein.

FIGS. 2A and 2B show gel electrophoresis results of the monomeric αS substrate corresponding to SEQ ID NO: 6 expressed in *E. coli* strain BL21(DE3) transformed using the plasmid represented by SEQ ID NO: 2, wherein FIG. 2A shows the results upon treatment with dithiothreitol ("DTT"), and FIG. 2B shows the results without treatment.

FIG. 3 shows gel electrophoresis results of the substrate expressed in *E. coli* strain BL21(DE3) transformed using the plasmid represented by SEQ ID NO: 4 before and after treatment with DTT and filtrations with 30 or 50 kDa filters.

FIG. 4A and FIG. 4B show αS-SAA "fast assay" aggregation curves (of three replicates individually) using the monomeric αS substrate corresponding to SEQ ID NO: 6 expressed in *E. coli* strain BL21(DE3) transformed using the plasmid represented by SEQ ID NO: 2, purified by acid precipitation to pH 4, in the presence of a confirmed PD sample (FIG. 4A) and in a healthy control (HC) (FIG. 4B).

FIG. 5A and FIG. 5B show αS-SAA "fast assay" aggregation curves (of three replicates individually) using the monomeric αS substrate corresponding to SEQ ID NO: 6 expressed in *E. coli* strain BL21(DE3) transformed using the plasmid represented by SEQ ID NO: 2, purified by acid precipitation to pH 3.5, in the presence of a confirmed PD sample (FIG. 5A) and in an HC (FIG. 5B).

FIG. 6A and FIG. 6B show αS-SAA "fast assay" aggregation curves (of three replicates individually) using the monomeric αS substrate corresponding to SEQ ID NO: 6 expressed in *E. coli* strain BL21(DE3) transformed using the plasmid represented by SEQ ID NO: 2, purified by acid precipitation to pH 3, in the presence of a confirmed PD sample (FIG. 6A) and in an HC (FIG. 6B).

FIG. 7A and FIG. 7B show αS-SAA "fast assay" aggregation curves (of three replicates individually) using the monomeric αS substrate corresponding to SEQ ID NO: 6 expressed in *E. coli* strain BL21(DE3) transformed using the plasmid represented by SEQ ID NO: 2, purified by acid precipitation to pH 2.5, in the presence of a confirmed PD sample (FIG. 7A) and in an HC (FIG. 7B).

FIG. 8A and FIG. 8B show αS-SAA "fast assay" aggregation curves (of three replicates individually) using the monomeric αS substrate corresponding to SEQ ID NO: 6 expressed in *E. coli* strain BL21(DE3) transformed using the plasmid represented by SEQ ID NO: 2, purified by acid precipitation to pH 2.0, in the presence of a confirmed PD sample (FIG. 8A) and in an HC (FIG. 8B).

FIGS. 9A-9D show αS-SAA "fast assay" aggregation curves (of three replicates individually) using the monomeric αS substrate corresponding to SEQ ID NO: 6 expressed in *E. coli* strain BL21(DE3) transformed using the plasmid represented by SEQ ID NO: 2, purified by acid precipitation to pH 2.5 and further supplemented with varying amounts of LPS, in the presence of confirmed PD samples (FIGS. 9A and 9C) and in HCs (FIGS. 9B and 9D).

Figure 11:
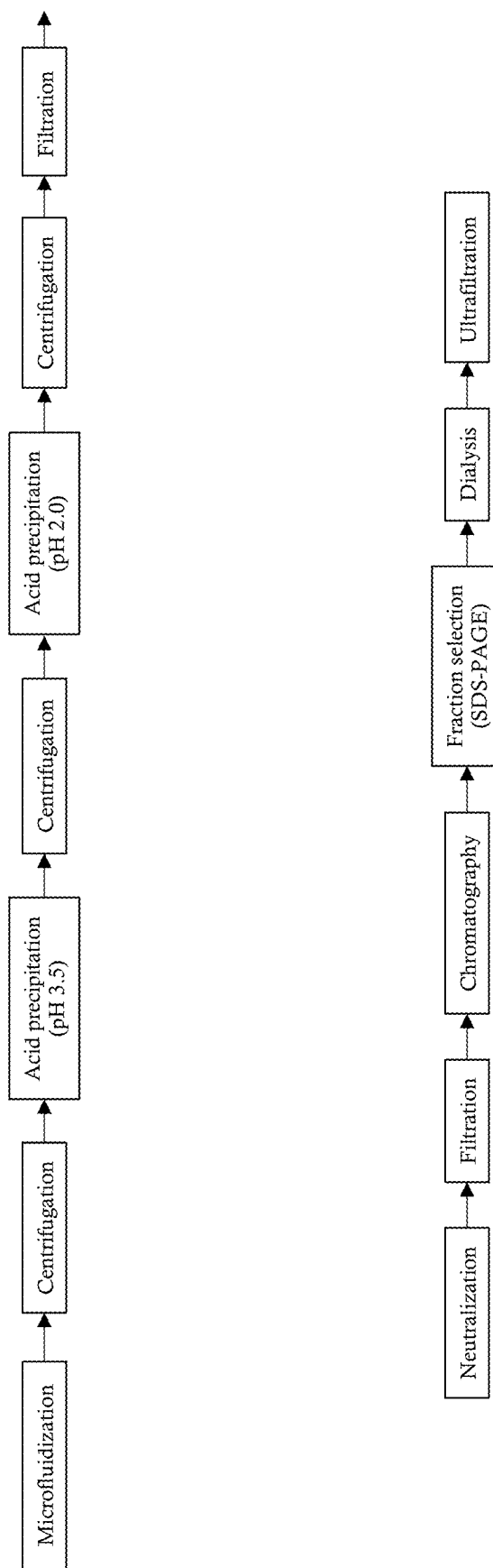
FIG. 11 shows a flowchart of an example method for purifying monomeric αS substrate that, together with proper SAA conditions, reduces, slows, or prevents altogether misfolding and self-aggregation when used in an αS-SAA assay, yet retains its activity in the presence of soluble, misfolded αS protein in a biological sample.
Figure 12A:
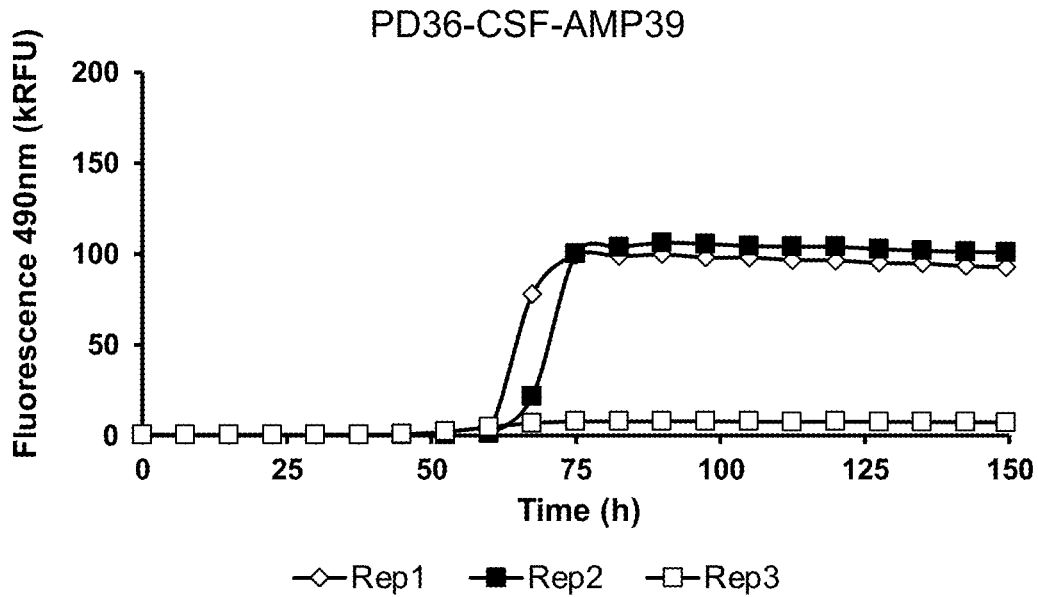
Figure 12B:
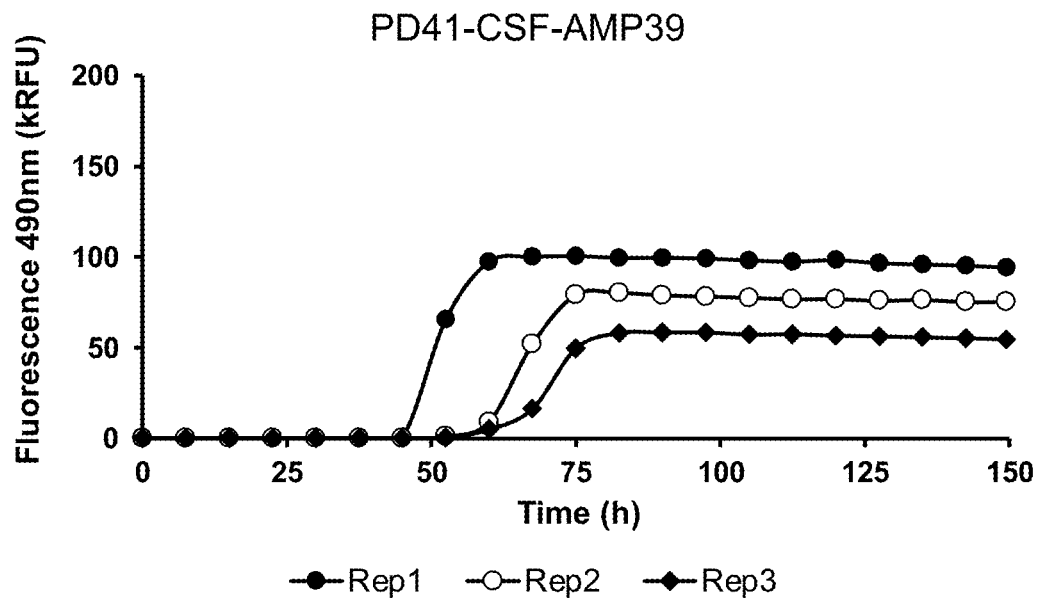
Figure 12C:
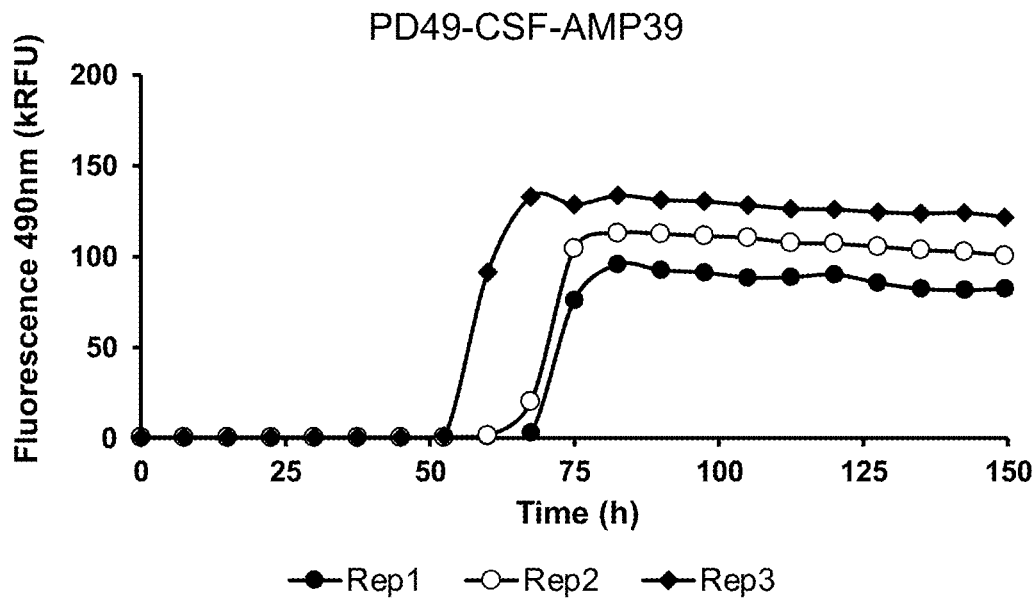
Figure 12D:
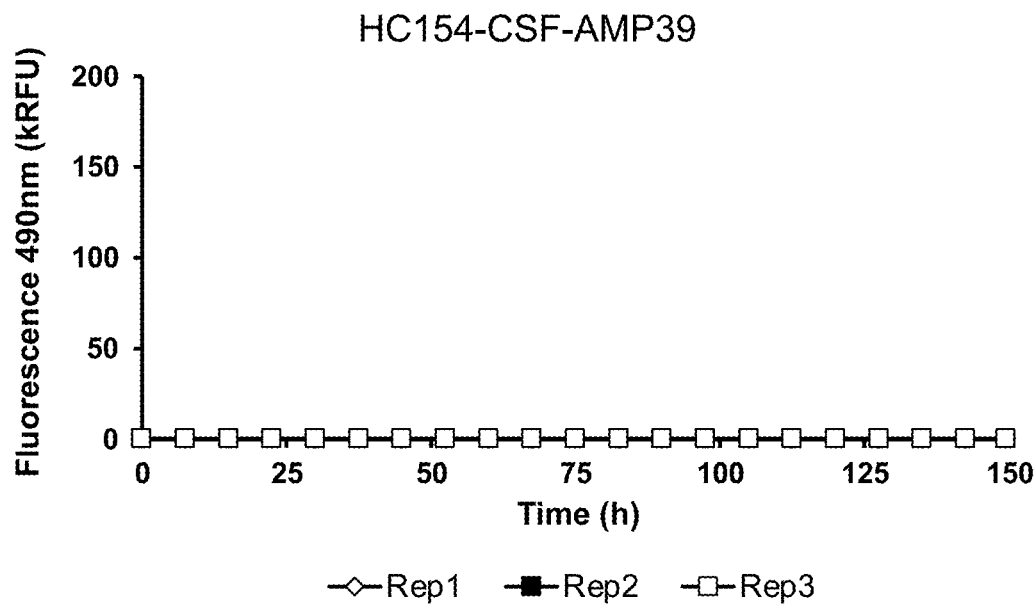

FIGS. 12A-12D show αS-SAA "fast assay" aggregation curves (of three replicates individually) using the monomeric αS substrate corresponding to SEQ ID NO: 6 expressed in *E. coli* strain BL21(DE3) transformed using the plasmid represented by SEQ ID NO: 2, purified by two acid precipitation steps—first at pH 3.5 and again at pH 2.0, as depicted in FIG. 11—in the presence of confirmed PD samples (FIGS. 12A-12C) and in an HC (FIG. 12D).

Figure 13A:
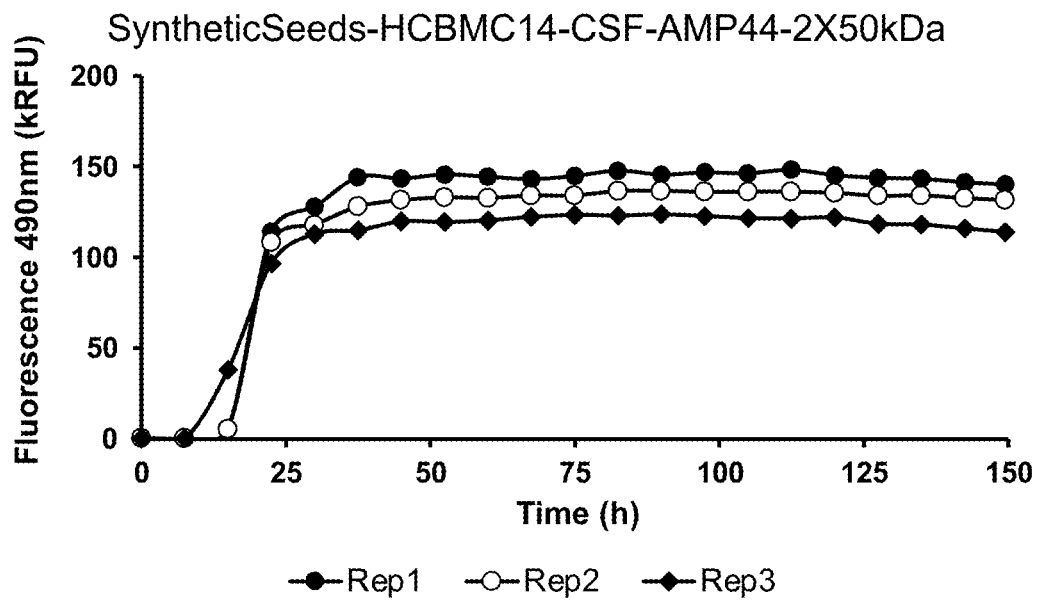
Figure 13B:
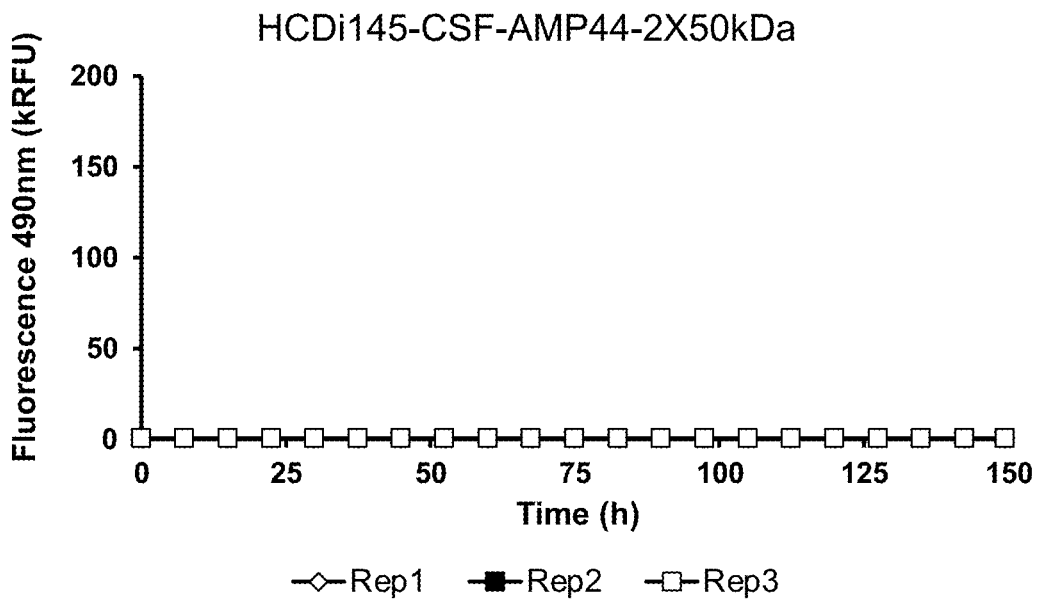
Figure 13C:
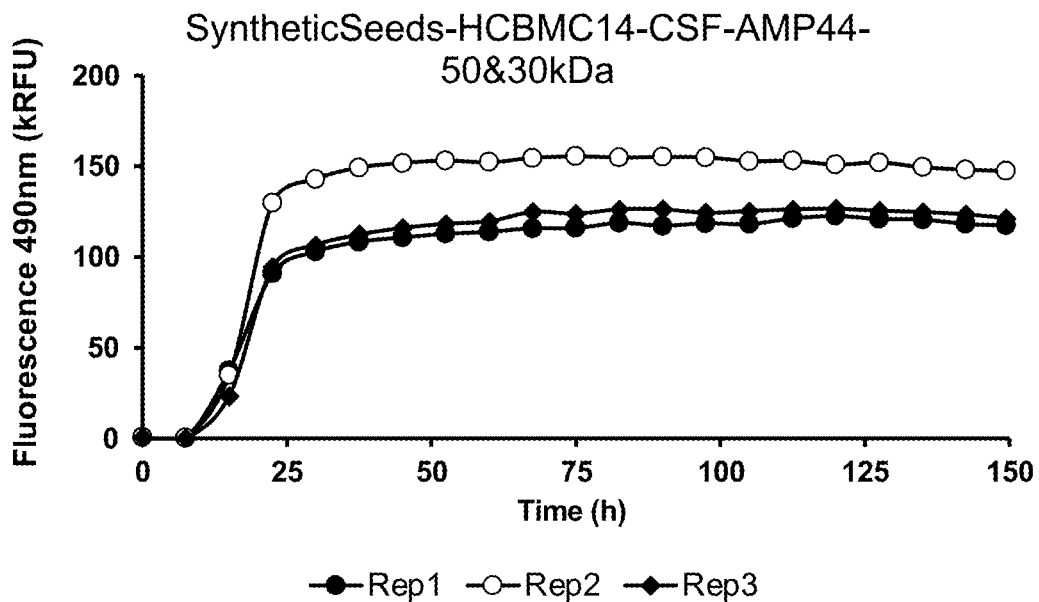
Figure 13D:
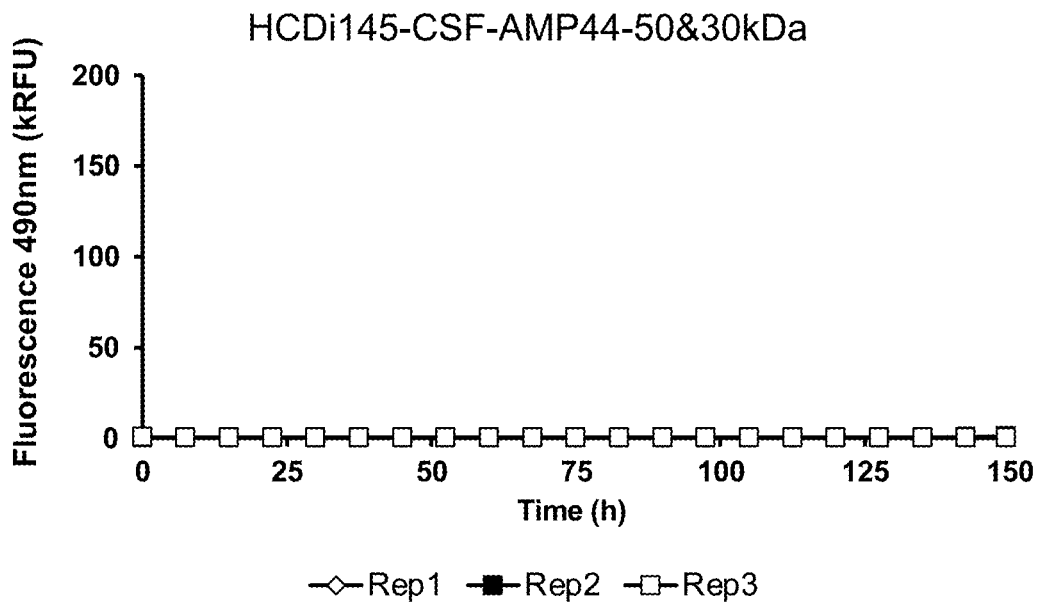

FIGS. 13A-13D show αS-SAA "fast assay" aggregation curves (of three replicates individually) using the monomeric αS substrate corresponding to SEQ ID NO: 6 expressed in *E. coli* strain BL21(DE3) transformed using the plasmid represented by SEQ ID NO: 2, purified by acid precipitation to pH about 3.1, and further purified by a second filtration of the dialyzed, filtered protein using a 50 kDa filter in the presence of synthetic seeds (FIG. 13A) and in an HC (FIG. 13B) or using a 30 kDa filter in the presence of synthetic seeds (FIG. 13C) and in an HC (FIG. 13D).

DETAILED DESCRIPTION

αS Expression Vector

An expression vector is provided for production of monomeric αS protein that, properly purified, exhibits a decreased tendency to self-aggregate in αS-SAA. The expression vector comprises a nucleic acid sequence coding for human αS protein or a conservative variant, the nucleic acid sequence comprising codons that have been optimized to produce human αS protein or a conservative variant when expressed by a suitable host cell. In one aspect, the host cell is an enterobacterial host cell such as *E. coli*. In another aspect the host cell is an S2 insect cell, a yeast cell, *Saccharomyces cerevisiae*, or *Pichia pastoris*. In some aspects, the codons have been optimized to avoid amino acid incorporation. In some aspects, the codons have been optimized to avoid cysteine misincorporation in the expressed protein. In further aspects, the codons have been optimized to avoid cysteine misincorporation in at least one of positions 39, 125, 133, and 136 of the expressed protein.

In one aspect, the expression vector may comprise a coding nucleic acid sequence represented by SEQ ID NO: 1 or having at least 90% identity with SEQ ID NO: 1. In one aspect, the expression vector may be a plasmid. For example, the expression vector may be a plasmid that enables the expression of a protein by means of the T7-lac operon system. In one aspect, the expression vector may be a plasmid comprising SEQ ID NO: 1, as represented by SEQ ID NO: 2 or having at least 90% identity with SEQ ID NO: 2.

Some amino acids can be coded for by more than one codon. A natural hierarchy exists for certain codons to be used in certain types of cells. Thus, a nucleic acid sequence configured for host cell expression of human αS protein may be different from a corresponding nucleic acid sequence that expresses human αS protein in human cells. For example, a nucleic acid sequence configured for expression of human αS protein in a microorganism such as *E. coli*, may include, e.g., substitution of bacteria-typical codons for human-typical codons for selected amino acids. For example, the nucleic acid sequence configured for expression of human αS protein in a microorganism such as *E. coli* may include a TAT codon expressing tyrosine rather than a TAC codon, which can lead to cysteine misincorporation.

SEQ ID NO: 1, upon expression in *E. coli*, mitigates misincorporation of, among other amino acids, cysteine for tyrosine at one or more of positions 39, 125, 133, and 136 in SEQ ID NO: 6 compared to expression of human native nucleic acid (e.g., via an expression vector comprising a coding nucleic acid sequence comprising SEQ ID NO: 3, as represented by SEQ ID NO: 4) in *E. coli*. Cysteine misincorporation, as opposed to misincorporation of other amino acids, is detectable because of the formation of dimers (see FIG. 3). Upon expression in the recombinant host cell, the αS protein (SEQ ID NO: 6) being produced has substantially decreased or no cysteine misincorporation at one or more of positions 39, 125, 133, and 136.

In various aspects, the expression vector may be operatively linked to regulatory sequences effective for expression of an optimized nucleic acid sequence (e.g., SEQ ID NO: 1) in the enterobacterial host cell. The term "operably linked" refers to the arrangement of various polynucleotide elements relative to each other such that the elements are functionally connected and can interact with each other. Such elements may include, without limitation, a promoter, an enhancer, a polyadenylation sequence, one or more introns and/or exons, and a coding sequence of a gene of interest to be expressed. The expression vector may be operatively linked to regulatory sequences effective for expression of the nucleic acid sequence represented by SEQ ID NO: 1 in *E. coli*. Many suitable vectors are available. The vector components generally include, but are not limited to, one or more of the following: an origin of replication, one or more marker genes, an enhancer element, a promoter, and a transcription termination sequence.

The αS protein may be recombinantly produced without modification or may be produced as a fusion polypeptide with a heterologous polypeptide, e.g., a signal sequence or other polypeptide having a specific cleavage site at the N-terminus of the mature protein or polypeptide. In general, the signal sequence may be a component of the vector, or it may be a part of the coding sequence that is inserted into the vector. In one aspect, the heterologous signal sequence selected may be one that is recognized and processed (i.e., cleaved by a signal peptidase) by the host cell.

Expression vectors usually contain a selection gene, also termed a selectable marker. The selection gene encodes a protein necessary for the survival or growth of transformed host cells grown in a selective culture medium. Host cells not transformed with the vector containing the selection gene will not survive in the culture medium. Typical selection genes encode proteins that: (a) confer resistance to antibiotics or other toxins, e.g., ampicillin, neomycin, methotrexate, or tetracycline; (b) complement auxotrophic deficiencies; or (c) supply critical nutrients not available from complex media.

Expression vectors will contain a promoter that is recognized by the host organism and is operably linked to an orthogonal protein coding sequence. Promoters are untranslated sequences located upstream (5') to the start codon of a structural gene (generally within about 100 to 1000 bp) that control the transcription of the particular nucleic acid sequence to which they are operably linked. Such promoters typically fall into two classes: inducible and constitutive. Inducible promoters are promoters that initiate increased levels of transcription from DNA under their control in response to some change in culture conditions, e.g., the presence or absence of a nutrient or a change in temperature. Many promoters recognized by a variety of potential host cells are well known.

In one aspect, the expression vector may comprise a coding nucleic acid sequence represented by SEQ ID NO: 1 or a nucleic acid sequence having a sequence identity percentage to SEQ ID NO: 1 of at least about 90, 91, 92, 93, 94, 95, 96, 97, 98, or 99. In some aspects, the nucleic acid sequence comprises a sequence having at least 95% identity with SEQ ID NO: 1. The nucleic acid sequence is not SEQ ID NO: 3.

The expression vector may be a plasmid. For example, the expression vector may be a plasmid represented by SEQ ID NO: 2. In some aspects, the plasmid nucleic acid sequence comprises a sequence having at least 95% identity with SEQ ID NO: 2. The plasmid nucleic acid sequence is not SEQ ID NO: 4.

To be clear, SEQ ID NO: 1 is the optimized DNA sequence that encodes for human αS with a C-terminal histag. SEQ ID NO: 1 is a part of SEQ ID NO: 2 (from 1459 to 1899 bp of SEQ ID NO: 2). SEQ ID NO: 2 is the DNA sequence of the whole vector or plasmid including SEQ ID NO: 1. SEQ ID NO: 3 is the non-optimized DNA sequence that encodes for human αS with a C-terminal histag. SEQ ID NO: 3 is part of SEQ ID NO: 4 (from 1459 to 1899 bp of SEQ ID NO: 4). SEQ ID NO: 4 is the DNA sequence of the whole vector or plasmid including SEQ ID NO: 3.

Due to the degenerate nature of the genetic code, a variety of different nucleotide sequences can be used to encode a given polypeptide. The present disclosure includes DNA compounds of any sequence that encode the amino acid sequences of the polypeptides described herein. In similar fashion, a polypeptide can typically tolerate one or more amino acid substitutions, deletions, and insertions in its amino acid sequence without loss or significant loss of a desired activity.

Nucleotide identity is determined by aligning the residues of the two polynucleotides to optimize the number of identical nucleotides along the lengths of their sequences. Gaps in either or both sequences are permitted in making the alignment in order to optimize the number of shared nucleotides, although the nucleotides in each sequence must nonetheless remain in their proper order. Preferably, two nucleotide sequences are compared using the Blastn program of the BLAST 2 search algorithm, as described by Tatusova, et al. (FEMS Microbiology Letters, 174, p. 247-50 (1999)), and available on the world wide web at the National Center for Biotechnology Information website, under BLAST in the Molecular Database section. Preferably, the default values for all BLAST 2 search parameters are used, including reward for match=1, penalty for mismatch=−2, open gap penalty=5, extension gap penalty=2, gap×dropoff=50, expect=10, wordsize=11, and optionally, filter on. In the comparison of two nucleotide sequences using the BLAST search algorithm, nucleotide identity is referred to as "identities."

Recombinant αS Protein-Producing Cells

A recombinant enterobacterial cell is also provided, wherein the cell comprises an expression vector for production of human αS protein or a conservative variant. The expression vector may comprise a nucleic acid sequence coding for human αS protein or a conservative variant, the nucleic acid sequence comprising codons that have been optimized to produce human αS protein or a conservative variant when expressed by the cell.

Enterobacteria, more formally known as Enterobacteriaceae, are a family of Gram-negative bacteria. Members of the Enterobacteriaceae family are bacilli (rod-shaped), are typically 1-5 μm in length, and usually include flagella for movement. Examples of enterobacteria include *E. coli*, *Salmonella*, *Klebsiella*, *Shigella*, *Enterobacter*, and *Citrobacter*.

In some aspects, the nucleic acid sequence coding for human αS protein or a conservative variant comprises codons that have been optimized to produce human αS protein or a conservative variant when expressed by an *E. coli* host cell, e.g., *E. coli* B121(DE3), BL21(DE3)-pLysS, and the like. *E. coli* needs to express the gene for T7 RNA polymerase under control of a lacUV5 promoter, allowing expression of the T7 RNA polymerase to be induced with IPTG or by autoinduction. Once T7 RNA polymerase is expressed, it enables the transcription of SEQ ID NO: 1 in the plasmid. BL21(DE3) cells have the required phenotype.

In various aspects, the expression vector included in the enterobacterial cell may include any of the features for an expression vector described herein. For example, in some aspects, the expression vector comprises a nucleic acid sequence having at least 95% identity with SEQ ID NO: 1. In further aspects, the recombinant αS protein expressed in the recombinant host cell is characterized by the absence of or mitigation of amino acid misincorporation, including cysteine misincorporation at one or more of positions 39, 125, 133, and 136.

The term "recombinant host cell" (or simply "host cell") refers to a cell (the particular subject cell and the progeny of such a cell) into which a recombinant vector has been introduced. Because certain modifications may occur in succeeding generations due either to mutation or environmental influences, the progeny may not, in fact, be identical to the parent cell, but are still included within the scope of the term "host cell." A recombinant host cell (e.g., a recombinant enterobacterial cell) may be an isolated cell, a cell line grown in culture, or may be a cell that resides in a living tissue or organism.

Methods for Preparing Monomeric αS Substrate

A method for preparing monomeric αS substrate for use in αS-SAA is also provided. The method comprises providing an enterobacterial host cell comprising a nucleic acid sequence coding for human αS protein or a conservative variant, the nucleic acid sequence comprising codons that have been optimized to produce human αS protein or a conservative variant; culturing the enterobacterial host cell under conditions effective to produce the human αS protein or a conservative variant; and obtaining the human αS protein or a conservative variant from the enterobacterial host cell. In some aspects, the method provides analogs or peptide fragments of human αS.

The phrases "monomeric αS protein" and "monomeric αS substrate" are used interchangeably and refer to one or more αS protein molecules or a conservative variant in their native, nonpathogenic configuration. In some aspects, the monomeric αS substrate comprises, consists essentially of, or consists of wildtype or recombinant human αS protein having 140 amino acids, having a molecular mass of 14,460 Da, and being represented by the sequence:

```
SEQ ID NO: 5:
MDVFMKGLSK AKEGVVAAAE KTKQGVAEAA GKTKEGVLYV
GSKTKEGVVH GVATVAEKTK EQVTNVGGAV VTGVTAVAQK
TVEGAGSIAA ATGFVKKDQL GKNEEGAPQE GILEDMPVDP
DNEAYEMPSE EGYQDYEPEA
```

In some aspects, the monomeric αS protein comprises, consists essentially of, or consists of a conservative variant of SEQ ID NO: 5. A conservative variant may be a peptide or amino acid sequence that deviates from SEQ ID NO: 5 only in the substitution or addition of one or several amino acids for amino acids having similar biochemical properties and having a minimal or beneficial impact on the activity of the resultant protein in the αS-SAA. A conservative variant must functionally perform substantially like the base component, i.e., SEQ ID NO: 5. For example, a conservative variant of SEQ ID NO: 5 will aggregate with misfolded αS protein and will form aggregates with substantially similar reaction kinetics as SEQ ID NO: 5 under similar reaction conditions.

Generally, a conservative variant (of SEQ ID NO: 5 or of any of the SEQ ID NOs disclosed herein) may have for example, one, two, three, four, five, six, seven (5%), and up to 14 (10%) substitutions, additions, or deletions in the amino acid sequence. In some aspects, the conservative variant of SEQ ID NO: 5 may include αS protein of other mammalian species, such as, for example, rodents and non-human primates. In some aspects, the conservative variant of SEQ ID NOs: 6-23 may include similarly tagged αS proteins of other mammalian species, such as, for example, rodents and non-human primates (that is, the variations is/are within the 140 amino acid sequence of the αS protein). In some aspects, the invention excludes SEQ ID NO: 5 as the monomeric αS substrate.

In some aspects, the monomeric αS substrate comprises a recombinant αS protein comprising six additional histidine amino acids (i.e., a polyHis purification tag) on the C-terminus of SEQ ID NO: 5, resulting in a molecular mass of 15,283 Da and being represented by the sequence:

```
SEQ ID NO: 6:
MDVFMKGLSK AKEGVVAAAE KTKQGVAEAA GKTKEGVLYV
GSKTKEGVVH GVATVAEKTK EQVTNVGGAV VTGVTAVAQK
TVEGAGSIAA ATGFVKKDQL GKNEEGAPQE GILEDMPVDP
DNEAYEMPSE EGYQDYEPEA HHHHHH
```

Thus, SEQ ID NO: 6 is distinguishable from SEQ ID NO: 5 by the six additional histidine amino acids on the C-terminus. The retention of the histidine tag may improve the ability of the human monomeric αS substrate to avoid self-aggregation. SEQ ID NO: 6 is further distinguishable from, e.g., a conservative variant of SEQ ID NO: 5 (and SEQ ID NO: 6) wherein one or more amino acids are added to the N-terminus. In some aspects, a conservative variant of SEQ ID NO: 5 wherein one or more amino acids are added to the N-terminus is excluded. However, some aspects include N-terminus additions. Thus:

```
SEQ ID NO: 7:
HHHHHH MDVFMKGLSK AKEGVVAAAE KTKQGVAEAA
GKTKEGVLYV GSKTKEGVVH GVATVAEKTK EQVTNVGGAV
VTGVTAVAQK TVEGAGSIAA ATGFVKKDQL GKNEEGAPQE
GILEDMPVDP DNEAYEMPSE EGYQDYEPEA
```

Additional purification tags are contemplated, including, e.g., FLAG, HA, Myc, and V5, thus generating the following SEQ ID NOs:

```
SEQ ID NO: 8:
MDVFMKGLSK AKEGVVAAAE KTKQGVAEAA GKTKEGVLYV
GSKTKEGVVH GVATVAEKTK EQVTNVGGAV VTGVTAVAQK
TVEGAGSIAA ATGFVKKDQL GKNEEGAPQE GILEDMPVDP
DNEAYEMPSE EGYQDYEPEA DYKDDDD

SEQ ID NO: 9:
DYKDDDD MDVFMKGLSK AKEGVVAAAE KTKQGVAEAA
GKTKEGVLYV GSKTKEGVVH GVATVAEKTK EQVTNVGGAV
VTGVTAVAQK TVEGAGSIAA ATGFVKKDQL GKNEEGAPQE
GILEDMPVDP DNEAYEMPSE EGYQDYEPEA

SEQ ID NO: 10:
MDVFMKGLSK AKEGVVAAAE KTKQGVAEAA GKTKEGVLYV
GSKTKEGVVH GVATVAEKTK EQVTNVGGAV VTGVTAVAQK
TVEGAGSIAA ATGFVKKDQL GKNEEGAPQE GILEDMPVDP
DNEAYEMPSE EGYQDYEPEA DYKDDDDK

SEQ ID NO: 11:
DYKDDDDK MDVFMKGLSK AKEGVVAAAE KTKQGVAEAA
GKTKEGVLYV GSKTKEGVVH GVATVAEKTK EQVTNVGGAV
VTGVTAVAQK TVEGAGSIAA ATGFVKKDQL GKNEEGAPQE
GILEDMPVDP DNEAYEMPSE EGYQDYEPEA

SEQ ID NO: 12:
MDVFMKGLSK AKEGVVAAAE KTKQGVAEAA GKTKEGVLYV
GSKTKEGVVH GVATVAEKTK EQVTNVGGAV VTGVTAVAQK
TVEGAGSIAA ATGFVKKDQL GKNEEGAPQE GILEDMPVDP
DNEAYEMPSE EGYQDYEPEA DYKDDDK

SEQ ID NO: 13:
DYKDDDK MDVFMKGLSK AKEGVVAAAE KTKQGVAEAA
GKTKEGVLYV GSKTKEGVVH GVATVAEKTK EQVTNVGGAV
VTGVTAVAQK TVEGAGSIAA ATGFVKKDQL GKNEEGAPQE
GILEDMPVDP DNEAYEMPSE EGYQDYEPEA

SEQ ID NO: 14:
MDVFMKGLSK AKEGVVAAAE KTKQGVAEAA GKTKEGVLYV
GSKTKEGVVH GVATVAEKTK EQVTNVGGAV VTGVTAVAQK
TVEGAGSIAA ATGFVKKDQL GKNEEGAPQE GILEDMPVDP
DNEAYEMPSE EGYQDYEPEA YPYDVPDYA
```

```
SEQ ID NO: 15:
YPYDVPDYA MDVFMKGLSK AKEGVVAAAE KTKQGVAEAA

GKTKEGVLYV GSKTKEGVVH GVATVAEKTK EQVTNVGGAV

VTGVTAVAQK TVEGAGSIAA ATGFVKKDQL GKNEEGAPQE

GILEDMPVDP DNEAYEMPSE EGYQDYEPEA

SEQ ID NO: 16:
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA YAYDVPDYA

SEQ ID NO: 17:
YAYDVPDYA MDVFMKGLSK AKEGVVAAAE KTKQGVAEAA

GKTKEGVLYV GSKTKEGVVH GVATVAEKTK EQVTNVGGAV

VTGVTAVAQK TVEGAGSIAA ATGFVKKDQL GKNEEGAPQE

GILEDMPVDP DNEAYEMPSE EGYQDYEPEA

SEQ ID NO: 18:
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA YDVPDYASL

SEQ ID NO: 19:
YDVPDYASL MDVFMKGLSK AKEGVVAAAE KTKQGVAEAA

GKTKEGVLYV GSKTKEGVVH GVATVAEKTK EQVTNVGGAV

VTGVTAVAQK TVEGAGSIAA ATGFVKKDQL GKNEEGAPQE

GILEDMPVDP DNEAYEMPSE EGYQDYEPEA

SEQ ID NO: 20:
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA EQKLISEEDL

SEQ ID NO: 21:
EQKLISEEDL MDVFMKGLSK AKEGVVAAAE KTKQGVAEAA

GKTKEGVLYV GSKTKEGVVH GVATVAEKTK EQVTNVGGAV

VTGVTAVAQK TVEGAGSIAA ATGFVKKDQL GKNEEGAPQE

GILEDMPVDP DNEAYEMPSE EGYQDYEPEA

SEQ ID NO: 22:
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA GKPIPNPLLGLDST

SEQ ID NO. 23:
GKPIPNPLLGLDST MDVFMKGLSK AKEGVVAAAE KTKQGVAEAA

GKTKEGVLYV GSKTKEGVVH GVATVAEKTK EQVTNVGGAV

VTGVTAVAQK TVEGAGSIAA ATGFVKKDQL GKNEEGAPQE

GILEDMPVDP DNEAYEMPSE EGYQDYEPEA
```

The preparation of monomeric αS substrate, polypeptide fragments thereof, mutants, truncations, derivatives, and splice variants that display substantially equivalent or altered αS activity relative to the wild-type protein are likewise contemplated. These variants may be deliberate, for example, such as modifications obtained through site-directed mutagenesis, or may be accidental, such as those obtained through mutations in hosts that are producers of the α-synuclein protein. Included within the scope of these terms are αS proteins specifically recited herein, and all substantially homologous analogs and allelic variants thereof.

Analogs may be made through conservative amino acid substitution. A "conservative amino acid substitution" may include, for example, one in which the amino acid residue is replaced with an amino acid residue having a similar side chain. Families of amino acid residues having similar side chains include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

A "non-essential" amino acid residue is a residue that can be altered from the wild-type sequence of αS without abolishing or, more preferably, without substantially altering αS's biological activity. Thus, a predicted non-essential amino acid residue in a αS protein is preferably replaced with another amino acid residue from the same side chain family. Alternatively, in another aspect, mutations can be introduced randomly along all or part of the αS coding sequence, such as by saturation mutagenesis, and the resultant mutants can be screened for αS biological activity to identify mutants that retain activity. Following mutagenesis of the nucleotide sequence for αS, the encoded protein can be expressed recombinantly, and the activity of the protein can be determined.

The monomeric αS substrates produced herein exhibit a decreased tendency to self-aggregate. In some aspects, the monomeric αS substrate does not self-aggregate under αS-SAA conditions. In other aspects, the monomeric αS substrate self-aggregates at a much lower level and/or at a much slower rate than the level or rate of self-aggregation of monomeric αS substrate obtained by previous methods of preparing monomeric αS substrate. In such aspects, the rate and/or level of self-aggregation can be 5%, 10%, 15%, 20%, 25%, 30%, 35%, 40%, 45%, 50%, 60%, 70%, 80%, or 90% or less compared to the level of aggregation of monomeric αS substrate obtained using methods other than those described herein. In other aspects, the monomeric αS substrate self-aggregates at a slower rate or lower level than the rate or level of aggregation of monomeric αS substrate with soluble, misfolded αS protein. In such examples, αS-SAA detection is still successful because a synucleinopathy-positive sample may be distinguished from mere self-aggregation of monomeric αS substrate by the intensity of the detection (relative fluorescence units) or the time period that fluorescence increase begins. The decreased self-aggregation for monomeric αS substrate described herein can be a result of differences in the method used to prepare the monomeric αS substrate, including differences in the resulting monomeric αS substrate composition.

The method of preparing human monomeric αS substrate or a conservative variant may comprise culturing a host cell comprising a nucleic acid sequence coding for human αS protein or a conservative variant, the nucleic acid sequence comprising codons that have been optimized to produce human αS protein or a conservative variant. Cells may be cultured in conventional nutrient media modified as appropriate for inducing promoters, selecting transformants, or amplifying the genes encoding the desired sequences. The culturing media may include buffers, nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH, and the like, are those previously used with the host cell selected for expression and will be apparent to the ordinarily skilled artisan. For a discussion of strategies for producing recombinant proteins using E. coli, see Gopal G., Kumar A., Protein J 32(6):419-25 (2013), the disclosure of which is incorporated herein by reference in its entirety.

The method of preparing monomeric αS substrate may include any of the expression vectors described herein. In some aspects, the enterobacteria is E. coli. In further aspects, the nucleic acid sequence of the expression vector comprises a sequence having at least 95% identity with SEQ ID NO: 1. In yet further aspects, the expression vector is a plasmid comprising a sequence having at least 95% identity with SEQ ID NO: 2. In additional aspects, the codons have been optimized to avoid amino acid incorporation, including cysteine misincorporation, in the expressed human αS protein or a conservative variant.

Once cells have been allowed to grow in culture for an appropriate amount of time (e.g., 4-24 hours), the cells are lysed and monomeric αS protein is purified from the lysed cells. A variety of methods may be used to lyse cells, such as use of a French press, sonication, freeze-thawing, chemical lysis, and microfluidizing. Purification may include a variety of different purification steps, such as centrifugation, column purification, dialysis, and acid precipitation to a pH of about 3.5 or less, optionally followed by addition of LPS and/or ultrafiltration (10 kDa to 300 kDa).

In some aspects, the method of preparing monomeric αS substrate from the host cell comprises lysing the cells using a microfluidizer. Microfluidizers break cells with high efficiency while maintaining intracellular content integrity by supplying constant, controlled shear rates, resulting in large cell membrane fragments that facilitate subsequent protein purification. Use of a microfluidizer for cell lysis can decrease the tendency of purified monomeric αS substrate to self-aggregate. An example of a suitable microfluidizer is the LM20 Microfluidizer® High Shear Fluid Homogenizer manufactured by Microfluidics.

The method of preparing monomeric αS substrate may comprise the step of separating the monomeric αS substrate from other components of the host cell such as lipids. In some aspects, obtaining the monomeric αS substrate from the host cell (e.g., E. coli) comprises contacting the monomeric αS substrate with Lipid Removal Agent ("LRA") to remove lipid contaminants (i.e., cell components). Thus, the monomeric αS substrate mixed with various other cell components is contacted with LRA after cell lysis, and the monomeric αS substrate is removed by centrifugation, which separates the protein from the lipids (the LRA and bound lipids go to the pellet fraction during centrifugation). Use of LRA for removal of the undesired lipid components may improve the ability of recombinant monomeric αS substrate in the resulting composition to avoid self-aggregation. LRA is a commercially available agent (available from Millipore Sigma) based on synthetic calcium silicate hydrate.

The method for preparing monomeric αS substrate or a monomeric αS substrate composition may comprise the step of initially separating the monomeric αS substrate from lipids, such as LPS, or nucleic acids, such as DNA and RNA. In some aspects, obtaining the monomeric αS substrate from the host cell (e.g., E. coli) comprises precipitation of non-synuclein components by addition of hydrochloric acid (HCl) to less than pH 3.50, including about pH 2.0 or lower. In some aspects, the method comprises adding LPS to the acid precipitated monomeric αS substrate.

In one aspect, obtaining the monomeric αS substrate from the host cell comprises precipitation of non-synuclein components by subjecting the human αS protein or a conservative variant to one or more acid precipitation steps at a pH of about 3.5 or less, e.g., first at pH 3.5 and again at pH 2, followed by chromatography, to yield the purified monomeric αS substrate or a conservative variant. An example of such an aspect is depicted by the flow chart shown in FIG. 11.

Options to remove contaminants such as metal-binding proteins (e.g., Ferric Uptake Regulatory Protein; FUR) from the monomeric αS substrate composition include iron-IMAC, antibody depletion, genomic modification of endogenous E. coli FUR to include a purification tag (other than histag or other purification tag used by the αS protein), iron saturation to reduce binding to the nickel column, or elimination washes with Fe++ during nickel-IMAC. In some aspects, purification of the monomeric αS substrate comprises excluding essentially all other proteins (e.g., metal-binding proteins). In further aspects, the metal-binding protein is a ferric uptake regulator (FUR).

αS Protein Compositions

The isolated human monomeric αS substrate or conservative variant composition can also include a suitable medium for suspending and/or storing the protein. For example, in some aspects, the monomeric αS substrate or conservative variant composition includes a buffer such as piperazine-N,N'-bis(2-ethanesulfonic acid) (PIPES) or phosphate buffered saline (PBS). In further aspects, the composition consists essentially of one of SEQ ID NOs: 5-23 and PIPES. The monomeric αS substrate may be substantially free of other materials such as lipid contaminant from the lysed enterobacterial cell.

In some aspects, the human monomeric αS substrate or conservative variant composition is purified so that it is essentially free of contaminants. Most of the contaminants found in the purified monomeric αS substrate or conservative variant are proteins of host cell origin, with only a few potential contaminants of human origin. MS/MS identifies proteins by detecting fragments after enzymatic digestion and comparing the fragment footprint to the footprints of known proteins, which are available in public databases. Thus, some fragments may match microorganisms other than the host cell (e.g., E. coli). However, most prokaryotic contaminating proteins will be from the host cell.

The resulting relative abundance of all human-originated proteins is extremely low compared to monomeric αS substrate. The most represented contaminants of human origin are cytochrome B5 and keratin related peptides.

As for the contaminants with bacterial origins, most are from the enterobacterial host cell (e.g., E. coli), which is the expression host. By far, the most likely and abundant bacterial contaminant appears to be FUR from *E. coli*. This protein has affinity for iron and is responsible for controlling iron's intracellular concentration. When iron is bound to FUR, the iron becomes capable of binding DNA and can act as a regulator. Since iron and nickel are both divalent cations, FUR's ability to bind iron is potentially the reason why FUR co-purifies with monomeric αS substrate during IMAC purification. αS-SAA competent monomeric αS substrate or conservative variant may contain lower concentration of FUR protein than self-aggregating substrate. The potential mechanism by which FUR induces self-aggregation could include ionic interaction between monomeric αS substrate and residual iron or nickel carried by FUR. The molecular weight of FUR is practically the same as αS, which may hide the contaminant in molecular weight based discriminating tools.

Some other notable contaminants from *E. coli* with relatively high abundance and matching scores are catabolite gene activator, HIT-like protein, FKBP-type peptidyl-prolyl cis-trans isomerase, and several ribosomal proteins. Catabolite gene activator is another DNA binding protein like FUR, but it does not require a metal cofactor. HIT proteins are proteins with histidine triad motifs that could be involved in binding zinc and have been shown to be able to bind nucleotides. Therefore, the triad motifs might also have affinity for nickel, which could make HIT proteins co-purify with monomeric αS substrate.

Accordingly, in some aspects, the human monomeric αS substrate or conservative variant composition is essentially free of other proteins. In some aspects, the other proteins comprise metal-binding proteins, while in further aspects the metal-binding proteins comprise FUR. Metal-binding proteins include proteins that bind (e.g., chelate) to metal ions such as sodium, potassium, magnesium, calcium, manganese, iron, cobalt, zinc, nickel, vanadium, molybdenum, and tungsten.

Potential contaminants of the human monomeric αS substrate or conservative variant composition, which are excluded from the composition in aspects of the invention, may include: Ferric uptake regulation protein OS=*Escherichia coli*; Catabolite gene activator OS=*Escherichia coli*; 30S ribosomal protein S12 OS=*Escherichia coli*; HIT-like protein hinT OS=*Escherichia coli*; FKBP-type peptidyl-prolyl cis-trans isomerase slyD OS=*Escherichia coli*; Bifunctional polymyxin resistance protein ArnA OS=*Escherichia coli*; 50S ribosomal protein L27 OS=*Escherichia coli*; Formyltetrahydrofolate deformylase OS=*Escherichia coli*; 30S ribosomal protein S15 OS=*Escherichia coli*; Glucosamine-fructose-6-phosphate aminotransferase [isomerizing] OS=*Escherichia coli*; Regulator of sigma D OS=*Escherichia coli*; Acyl-[acyl-carrier-protein]-UDP-N-acetylglucosamine O-acyltransferase OS=*Escherichia coli*; UPF0047 protein yjbQ OS=*Escherichia coli*; Arabinose 5-phosphate isomerase GutQ OS=*Escherichia coli*; 50S ribosomal protein L28 OS=*Escherichia coli*; 30S ribosomal protein S16 OS=Parabacteroides *distasonis*; 30S ribosomal protein S20 OS=*Escherichia coli*; Arabinose 5-phosphate isomerase KdsD OS=*Escherichia coli*; 30S ribosomal protein S2 OS=*Escherichia coli*; 50S ribosomal protein L7/L12 OS=*Kineococcus radiotolerans*; Ribosomal RNA large subunit methyltransferase A OS=*Escherichia coli*; Nucleoside diphosphate kinase OS=*Alcanivorax borkumensis*; Uncharacterized HTH-type transcriptional regulator yeiE OS=*Escherichia coli*; 30S ribosomal protein S7 OS=*Escherichia coli*; NADH-quinone oxidoreductase subunit B OS=*Geobacter* sp.; NADH-quinone oxidoreductase subunit B OS=*Jannaschia* sp.; 30S ribosomal protein S16 OS=*Bacteroides thetaiotaomicron*; Elongation factor Tu OS=*Actinobacillus pleuropneumoniae* serotype 3; 50S ribosomal protein L4 OS=*Acinetobacter* sp.; 50S ribosomal protein L25 OS=*Caldicellulosiruptor saccharolyticus*; Spermidine N(1)-acetyltransferase OS=*Escherichia coli*; 50S ribosomal protein L4 OS=*Neisseria meningitidis* serogroup C; Aminoglycoside 3'-phosphotransferase OS=*Escherichia coli*; Putative uncharacterized protein yghX OS=*Escherichia coli*; N-hydroxyarylamine 0-acetyltransferase OS=*Escherichia coli*; Outer membrane protein A OS=*Escherichia coli*; Ribosomal RNA small subunit methyltransferase H OS=*Thermoanaerobacter tengcongensis*; Ribosomal RNA small subunit methyltransferase H OS=*Clostridium acetobutylicum*; Phosphoribosylformylglycinamidine cyclo-ligase OS=*Geobacillus* sp.; Uncharacterized protein yhbW OS=*Escherichia coli*; Putative acyl-[acyl-carrier-protein] desaturase desA1 OS=*Mycobacterium tuberculosis*; Riboflavin biosynthesis protein RibD OS=*Escherichia coli*; Ribosomal RNA large subunit methyltransferase G OS=*Escherichia coli*; Bifunctional protein putA OS=*Escherichia coli*; NADH-quinone oxidoreductase subunit G OS=*Escherichia coli*; D-amino acid dehydrogenase small subunit OS=*Azotobacter vinelandii*; Peptidase T OS=*Erwinia carotovora* subsp. atroseptica; Cobyrinic acid A,C-diamide synthase OS=*Rhodobacter capsulatus*; ATP synthase subunit beta OS=*Rickettsia akari*; UPF0371 protein M6_Spy1067 OS=*Streptococcus pyogenes* serotype; NAD-reducing hydrogenase hoxS subunit alpha OS=*Cupriavidus necator*; Chaperone protein DnaK OS=*Escherichia coli*; Urease subunit alpha OS=*Yersinia enterocolitica* serotype; 1-deoxy-D-xylulose-5-phosphate synthase OS=*Bordetella avium*; and Translation initiation factor IF-2 OS=*Proteus vulgaris*.

Methods for Using Monomeric αS Substrate in SAA

Human monomeric αS substrate or conservative variant compositions described herein having a decreased tendency to self-aggregate are useful as substrate proteins in αS-SAA. Example αS-SAA methods include those disclosed in US20160077111A1 ("slow assay"), US20210063416A1 ("fast assay"), and U.S. Nonprovisional patent application Ser. No. 17/154,966.

Examples have been included to explain more clearly particular aspects of the invention.

EXAMPLES

Example 1: Synthesis of Recombinant Monomeric αS Substrate SEQ ID NO: 6 Using SEQ ID NO: 2

*E. coli* BL21(DE3) was transformed according to the manufacturer's instructions (Lucigen® E. Cloni® Express Chemically Competent Cells, MA019 Rev. 31 Oct. 2016) with the expression vector comprising the plasmid represented by SEQ ID NO: 2. This plasmid comprises a codon optimized nucleic acid sequence represented by SEQ ID NO: 1, which encodes for the C-terminal HisTag αS protein represented by SEQ ID NO: 6 without amino acid misincorporation.

Bacterial pellets were grown in-house overnight using autoinduction media. Pellets were tested for inclusion bodies using B-Per reagent and SDS-PAGE. αS protein represented by SEQ ID NO: 6 was highly expressed (~30% of all protein) and there were no inclusion bodies detected by B-Per. SEQ ID NO: 1 was verified by DNA sequencing.

Example 2: Purification of αS Protein by Microfluidization and Acid Precipitation The bacterial pellets containing αS protein were prepared as described in Example 1, washed, frozen at −80° C., and stored until use. For purification, the cells were thawed in a water bath set to 30° C. for 40-45 min in lysis buffer (50 mM NaH2PO4 pH: 8.0, 0.3M NaCl, 0.2 mM EDTA, 20 mM Imidazole, 1 mM PMSF, 0.1 mM TCEP). The cells were resuspended in a final volume of lysis buffer equivalent to 4× the weight of the pellet (80 mL lysis buffer to 20 g of pellet). The resuspended cells were degassed using a standard vacuum pump. The resuspended cells were lysed by a microfluidizer (LM20 Microfluidizer®). The crude lysate was clarified by centrifugation to remove large cellular debris.

The clarified lysate was titrated by stepwise addition of 1M HCl during agitation. After reaching a target pH, the acidified lysate was incubated with agitation for 20-60 min. The acidified lysate was clarified by centrifugation, and the supernatant was neutralized using 1M NaOH to pH 8.00. The neutralized lysate was filtered by 0.22 µm filters, and the material was loaded onto a column with nickel-Sepharose resin.

Chromatography was carried out using standard protocols. After loading the neutralized filtered lysate, the packed column was washed with a first wash buffer (50 mM NaH2PO4 pH: 7.4, 0.5M NaCl, 20 mM Imidazole, 0.1 mM TCEP) and a second wash buffer (50 mM NaH2PO4 pH: 7.4, 0.15M NaCl, 20 mM Imidazole, 0.1 mM TCEP). Protein was eluted with elution buffer (50 mM NaH2PO4 pH: 7.4, 0.15M NaCl, 250 mM Imidazole, 0.1 mM TCEP), and elution fractions were collected on ice. The elution fractions were evaluated by SDS-PAGE and Coomassie staining to determine the fractions with the lower amounts of contaminants and higher amounts of recombinant αS protein.

After pooling the elution fractions with high αS and low contaminants, the pool was dialyzed for 4-5 h in 1×PBS at a dilution factor of 1:200. A second dialysis was performed (1:400) overnight for a total 1:80,000 dilution factor.

The dialyzed material was filtered using a 50,000 Dalton MWCO Amicon centrifugal device. The 50 kDa filtered material is the final αS monomer product, and protein concentration was determined by BCA, A280, or a combination of A280 and BCA for increased accuracy. The protein was aliquoted into single use aliquots containing around 6.5 mg each.

Figure 1:
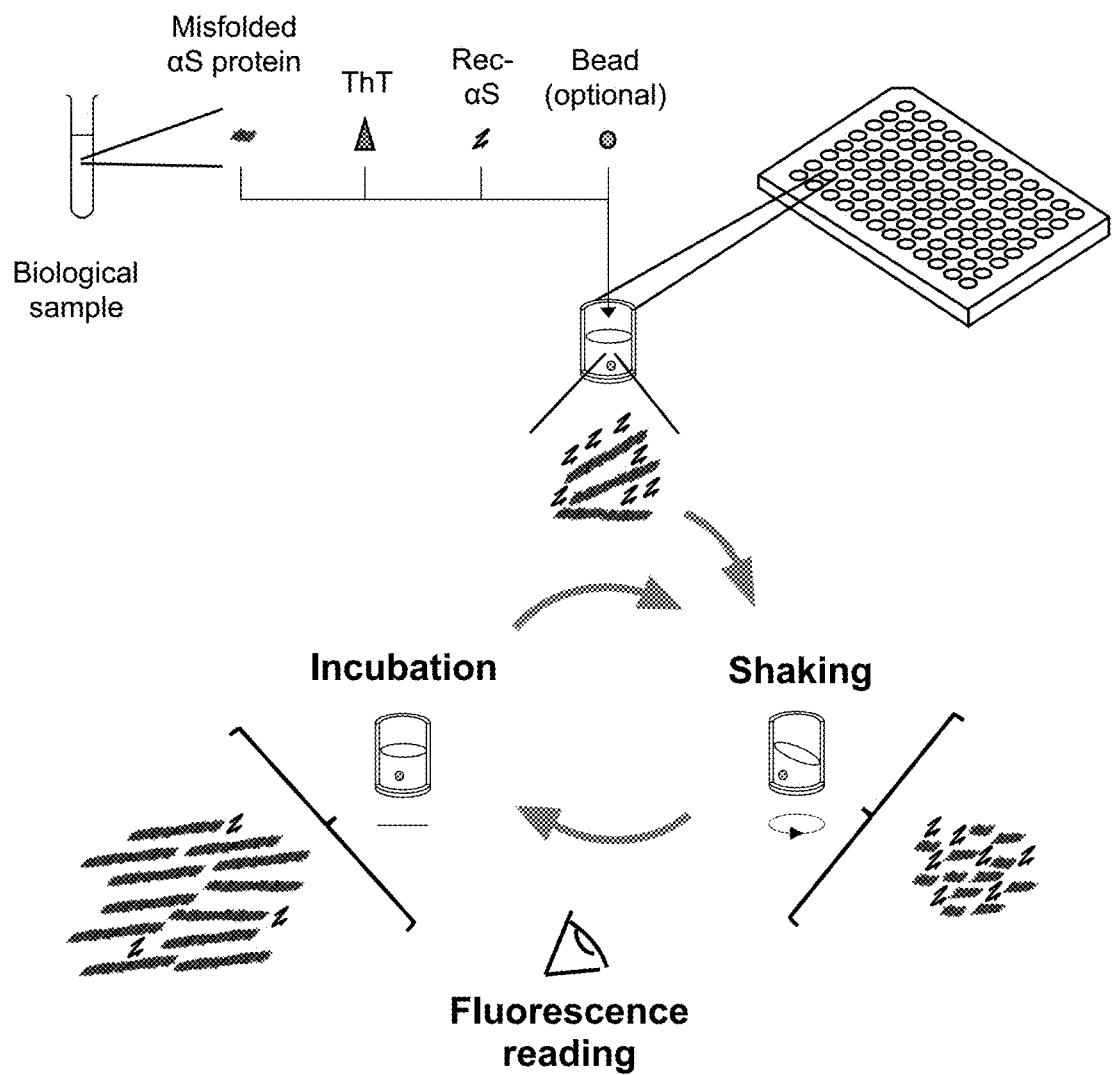
Figures 2A, 2B:
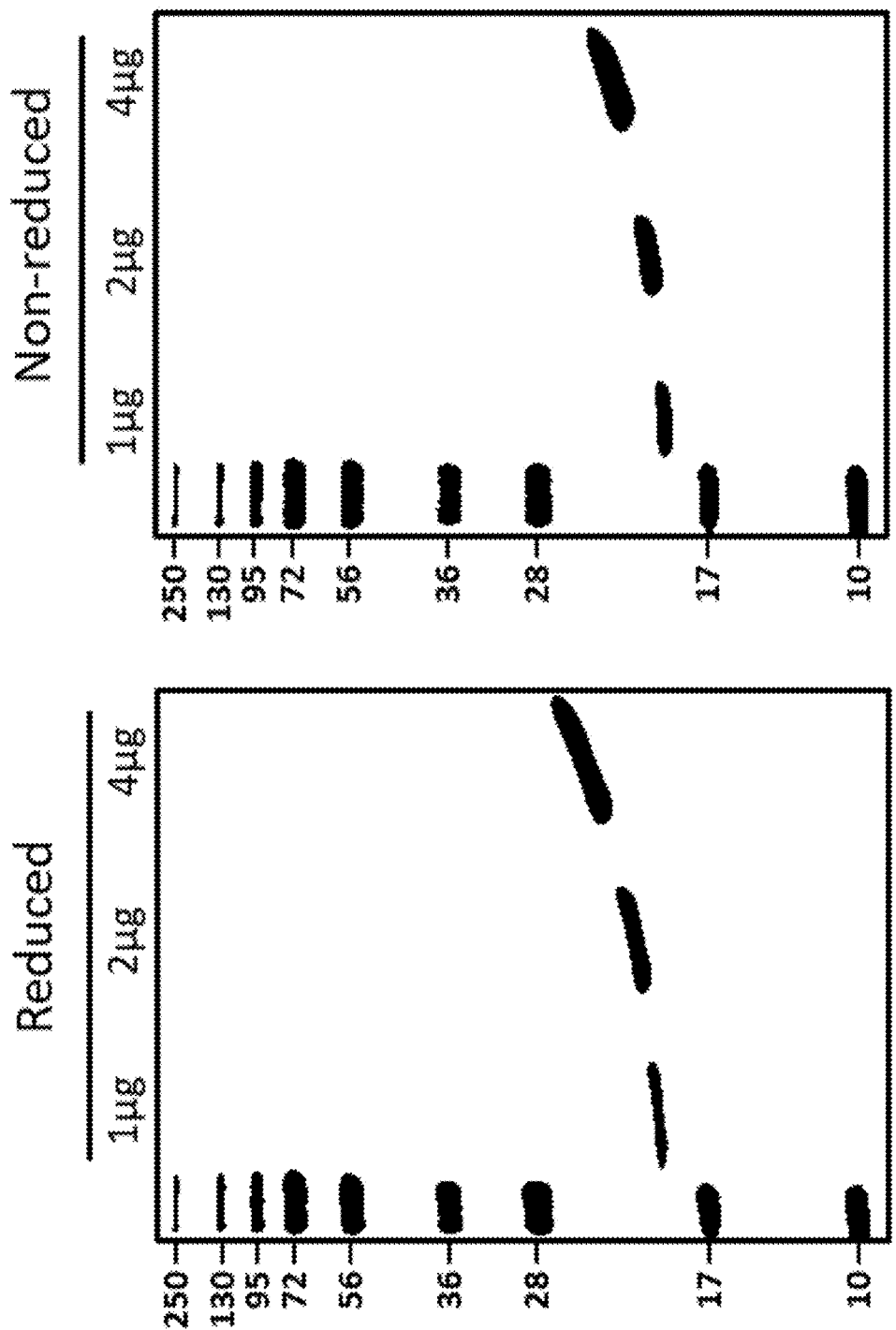

FIGS. 2A and 2B show electrophoresis results for C-terminal HisTag αS protein (SEQ ID NO: 6) prepared using the plasmid (SEQ ID NO: 2) comprising the nucleotide sequence (SEQ ID NO: 1). The C-terminal HisTag αS protein aliquot was separated into two fractions. One fraction of the C-terminal HisTag αS protein aliquot was contacted with DTT under disulfide bond reducing conditions. As shown in FIGS. 2A and 2B, the reduced and non-reduced fractions, respectively, of the C-terminal HisTag αS protein were essentially identical when run at protein amounts per lane of 1 µg, 2 µg, and 4 µg. No band corresponding to dimer formation was visible. Accordingly, the plasmid (SEQ ID NO: 2) comprising the nucleotide sequence (SEQ ID NO: 1) produces the cysteine misincorporation-free C-terminal HisTag αS protein sequence (SEQ ID NO: 6) when expressed in *E. coli*.

Figure 3:
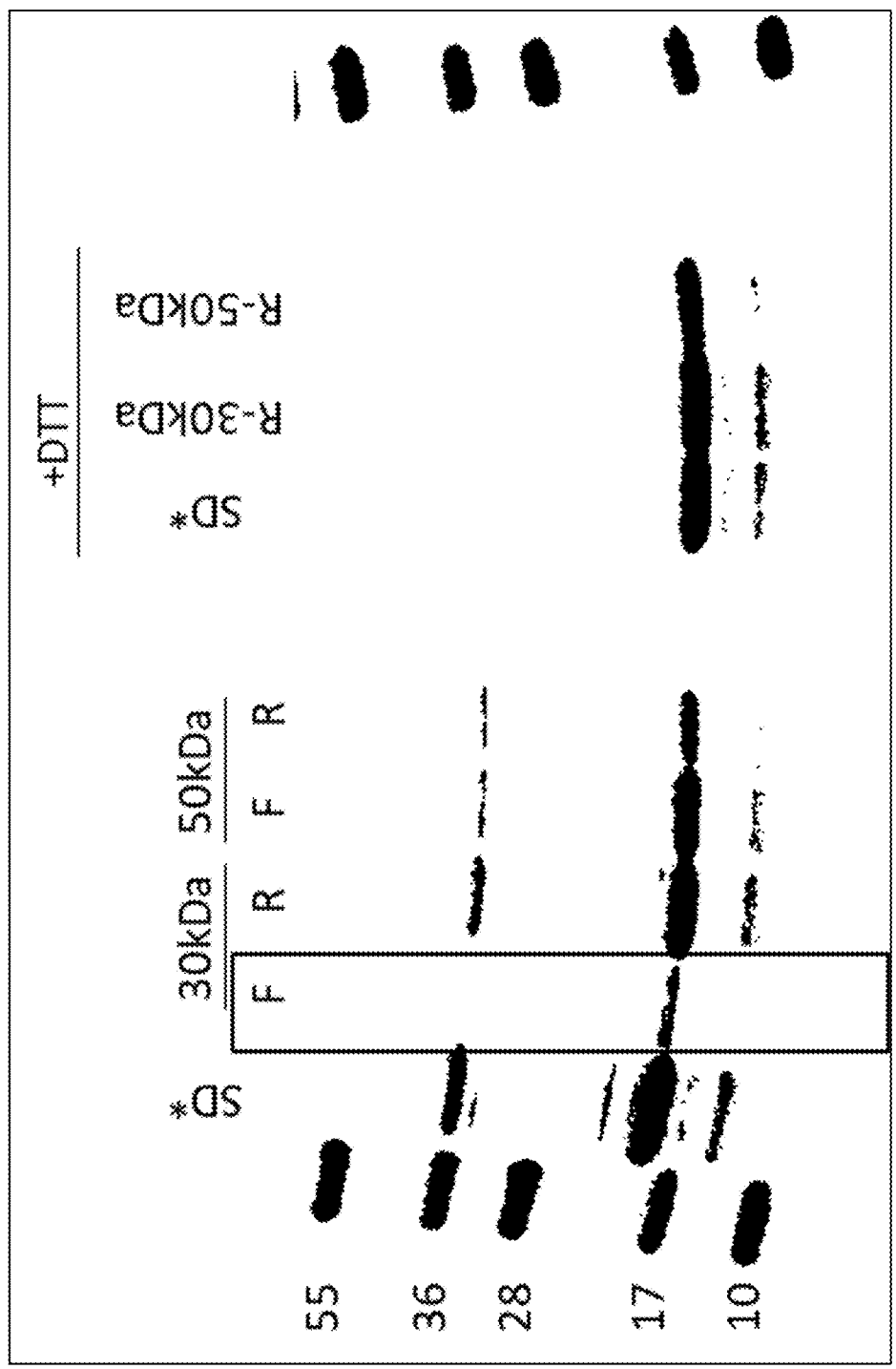

Comparative Example 1: Gel Electrophoresis of Recombinant Human Monomeric αS Substrate Prepared without Using Optimized Codons FIG. 3 shows electrophoresis results for C-terminal HisTag αS protein (intending SEQ ID NO: 6, but because of cysteine misincorporation, likely comprising a mix of SEQ ID NO: 6 and SEQ ID NO: 6-Y136C) prepared using the plasmid (SEQ ID NO: 4) comprising the nucleotide sequence (SEQ ID NO: 3) before and after treatment with DTT. Lane 1 (the first lane from the left) shows various molecular weight fractions of an incubation mixture. Lane 2 shows the recombinant monomeric αS protein reagent (SD*). Lane 3 shows the filtrate (F) through a 30 kDa cutoff filter. Lane 4 shows the retentate (R) caught by the 30 kDa cutoff filter. Lane 5 shows the filtrate through a 50 kDa cutoff filter. Lane 6 shows the retentate caught by the 50 kDa cutoff filter. The C-terminal HisTag αS protein has a nominal molecular weight of ~15 kDa, but it runs slightly higher than the 17 kDa marker in SDS-PAGE. Accordingly, electrophoresis of the filtrate through the 30 kDa cutoff filter in Lane 3 showed a band at ~15 kDa, corresponding to the C-terminal HisTag αS protein. In addition to the intended 15 kDa recombinant monomeric folded αS protein, FIG. 3, Lanes 4, 5, and 6 showed a band at ~36 kDa. After treatment of with DTT, the band at ~36 kDa disappeared, leaving only the expected band at ~15 kDa, indicating the presence and separation of dimers into monomers.

Example 3: αS-SAA of the Acid Precipitated Monomeric αS Substrate

αS-SAA using the acid precipitated αS monomer was conducted by the "fast assay" procedure, using the following parameters:

| Parameter | Fast Assay (FA) |
| --- | --- |
| Buffer ([ ] (mM) and pH) | 100 mM PIPES pH 6.50 |
| [NaCl] (mM) | 500 |
| ThT (µM) | 10 |
| Substrate | Recombinant C-terminal hi stag αSyn (MW = 15,283 mg/mmol) (SEQ ID NO: 6) |
| [substrate] (µM) | 19.6 µM |
| [substrate] (mg/mL) | 0.3 |
| Sample (µL) | 40 |
| Shaking type | Orbital |
| Shaking speed (rpm) | 600-800 |
| Shaking time (min) | 1 |
| Incubation time (min) | 29 |
| Beads material | Si3N4 |
| Beads size (mm) | 2.38 |
| Amount of beads | 1 (ea) |
| Temperature (° C.) | 37 |
| Reaction volume (µL) | 200 |

Figure 4A:
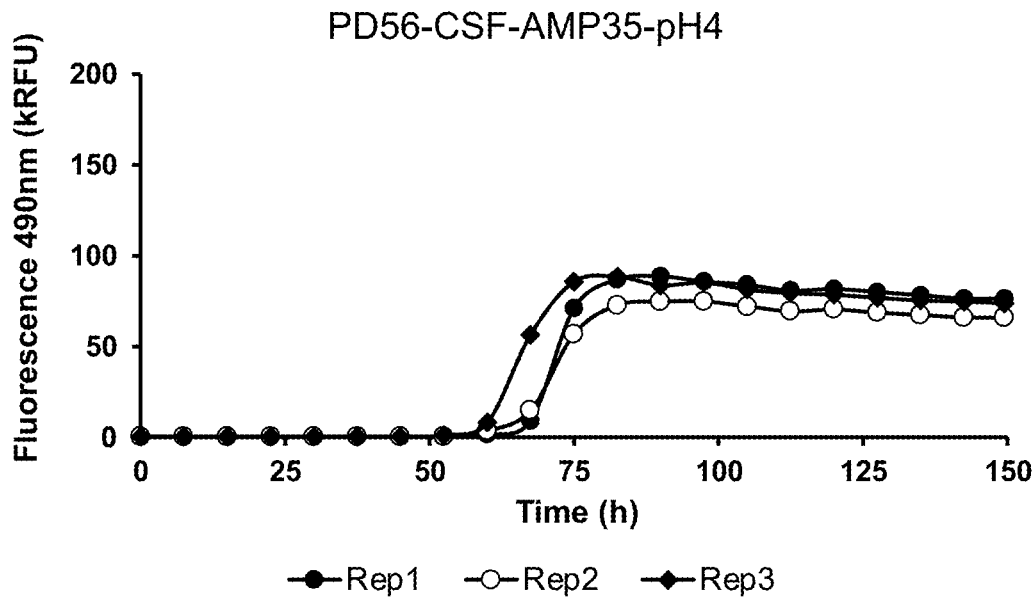
Figure 4B:
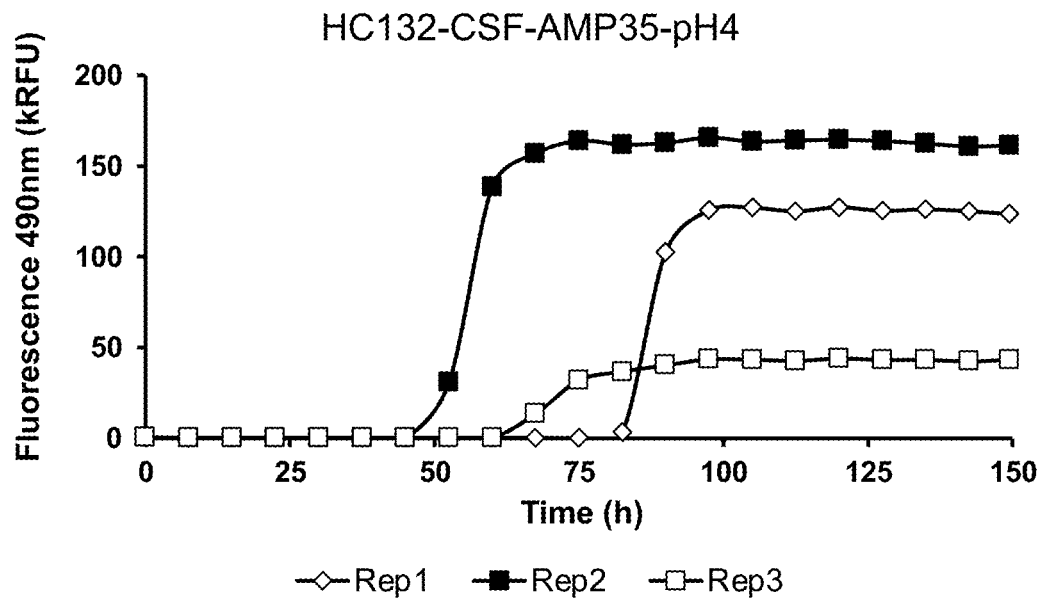

FIG. 4A shows αS-SAA "fast assay" aggregation curves (of three replicates individually) in the presence of a confirmed PD sample, where the monomeric αS substrate was purified by acid precipitation to pH 4. The monomeric αS substrate aggregated as expected in the presence of the PD sample, reaching Fmax between 60-70 hours. However, the monomeric αS substrate showed high propensity for self-aggregation when analyzing a CSF sample from a HC (FIG. 4B).

Figure 5A:
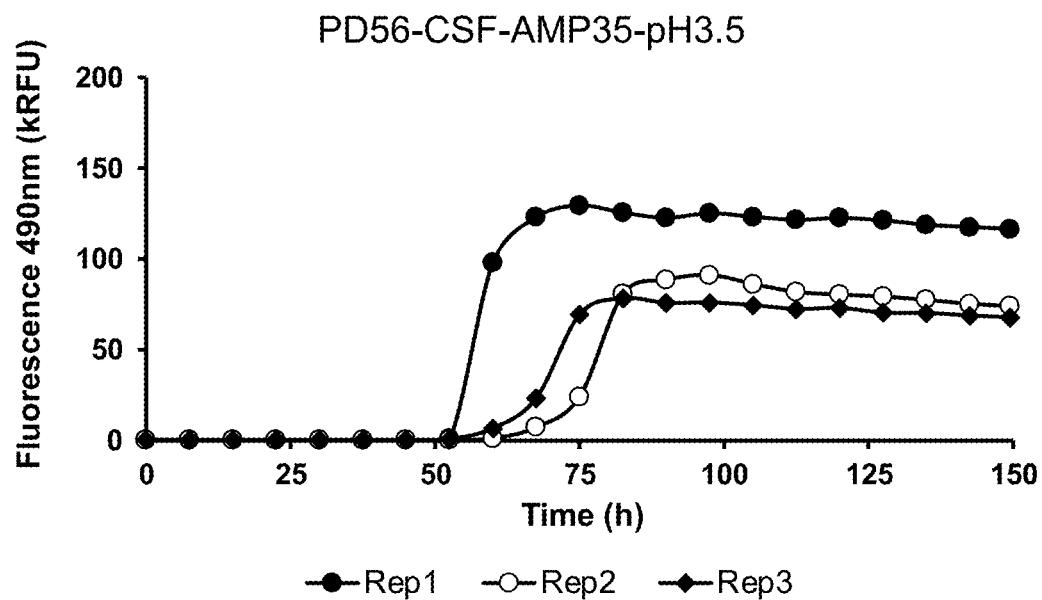
Figure 5B:
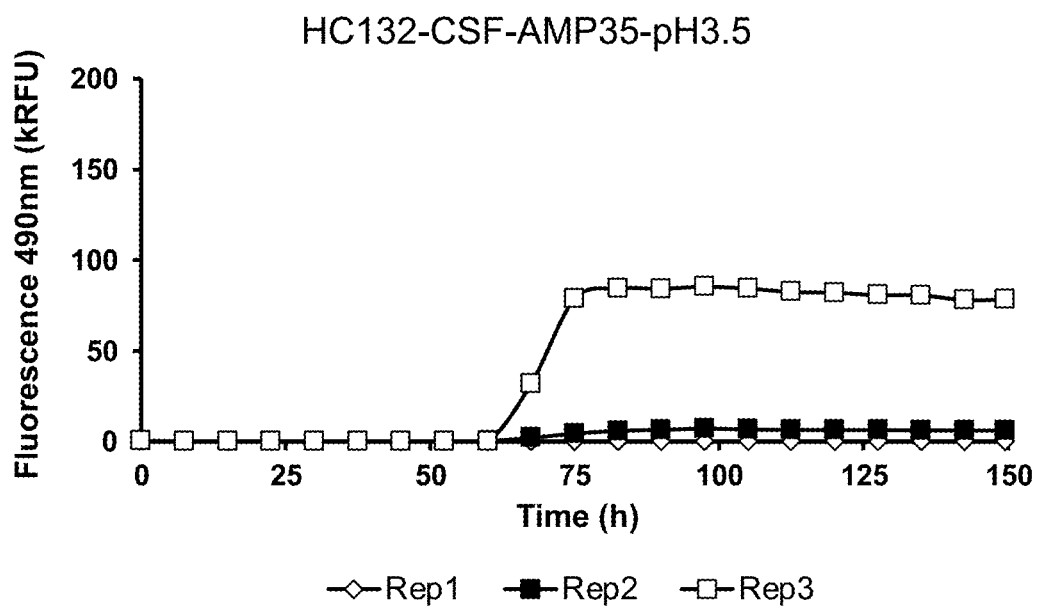

Likewise, FIG. 5A shows αS-SAA "fast assay" aggregation curves (of three replicates individually) in the presence of a confirmed PD sample, where the monomeric αS substrate was purified by acid precipitation to pH 3.5. The monomeric αS substrate aggregated as expected in the presence of the PD sample, reaching Fmax between 60-70 hours, but showing greater variability than with the substrate produced using pH 4.0 acid precipitation. The monomeric αS substrate showed medium self-aggregation with an HC (FIG. 5B).

Figure 6A:
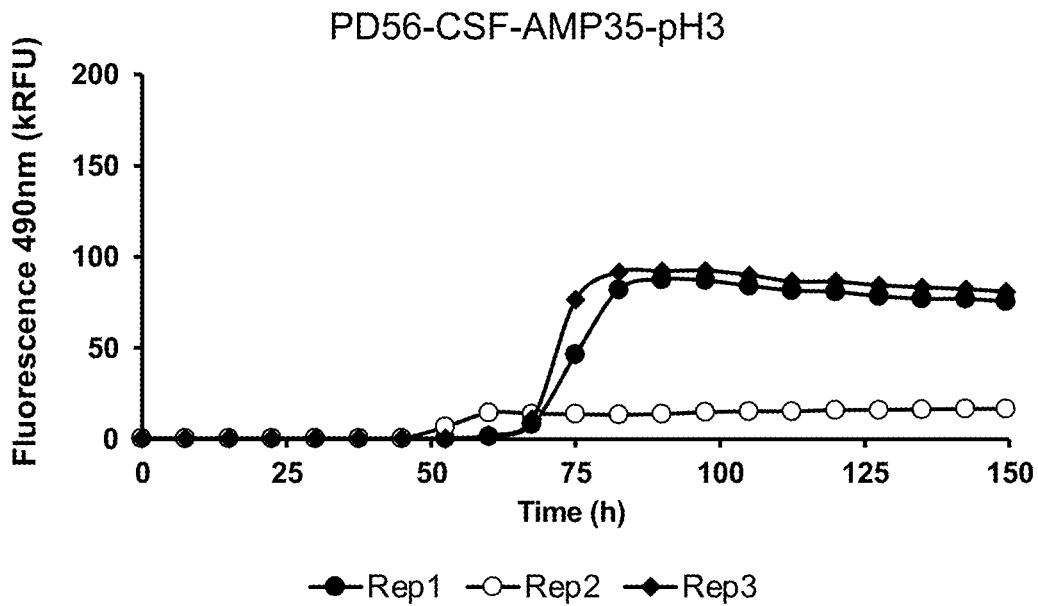
Figure 6B:
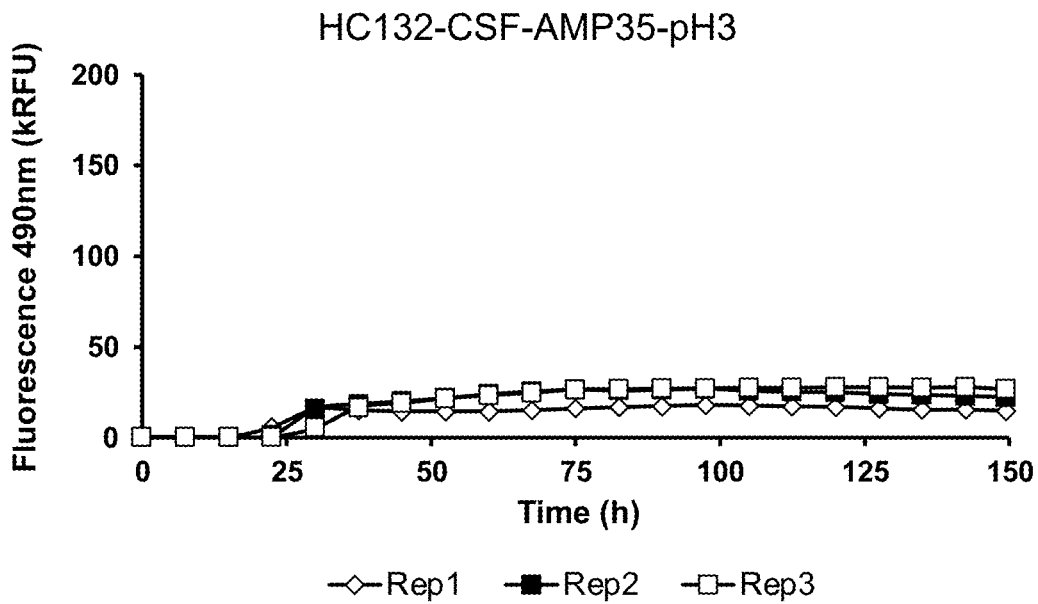

FIG. 6A shows αS-SAA "fast assay" aggregation curves (of three replicates individually) in the presence of a confirmed PD sample, where the monomeric αS substrate was purified by acid precipitation to pH 3. At pH 3, the PD aggregation is as expected for only two of the three wells. The third well showed a much lower fluorescence, which might be explained by self-aggregation. More surprisingly, the HC (FIG. 6B) was "reproducibly positive," indicating that the substrate purified in this way is more prone to self-aggregation (and further supporting the hypothesis that the third replicate from the PD sample could be self-aggregation).

Figure 7A:
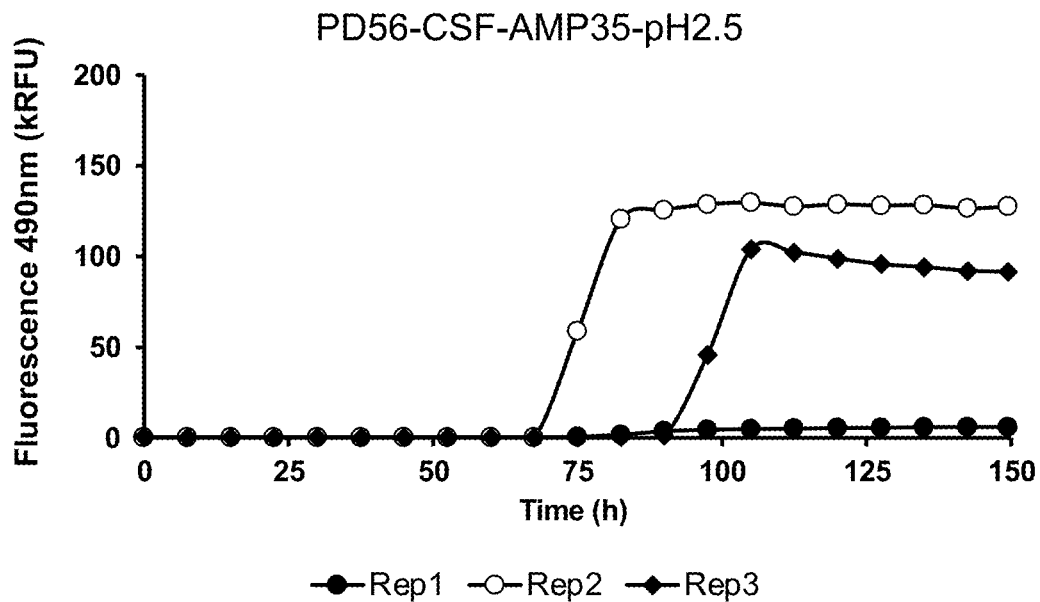
Figure 7B:
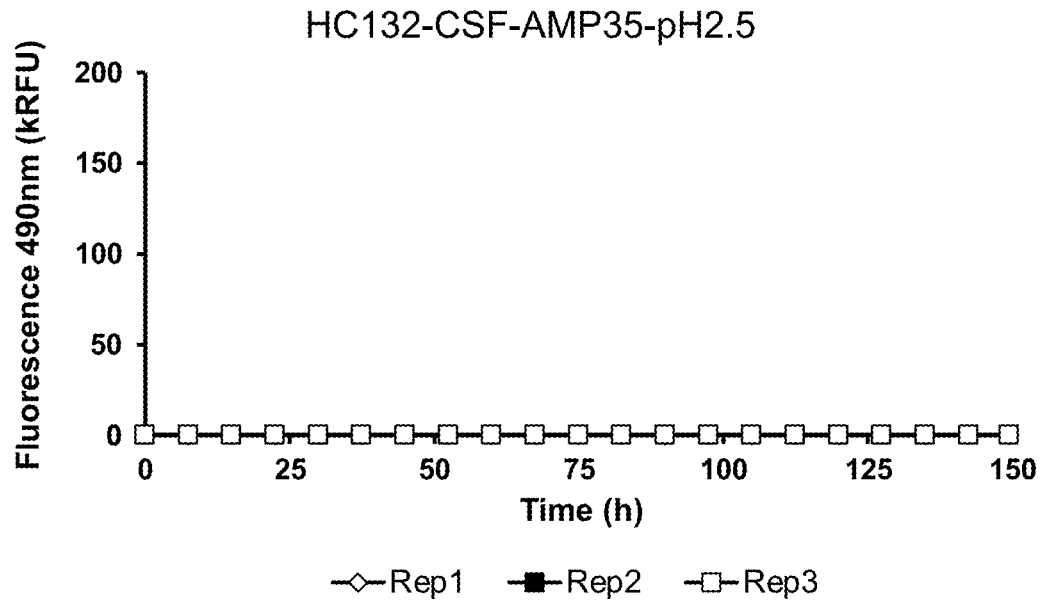

FIG. 7A shows αS-SAA "fast assay" aggregation curves (of three replicates individually) in the presence of a confirmed PD sample, where the monomeric αS substrate was purified by acid precipitation to pH 2.5. Strikingly, PD aggregation was heavily affected in terms of poor reproducibility, delayed aggregation of the positive wells (75-90 hours), and lack of amplification for one of the replicates, which could generate a false negative result. Conversely, the monomeric αS substrate did not self-aggregate (FIG. 7B).

Figure 8A:
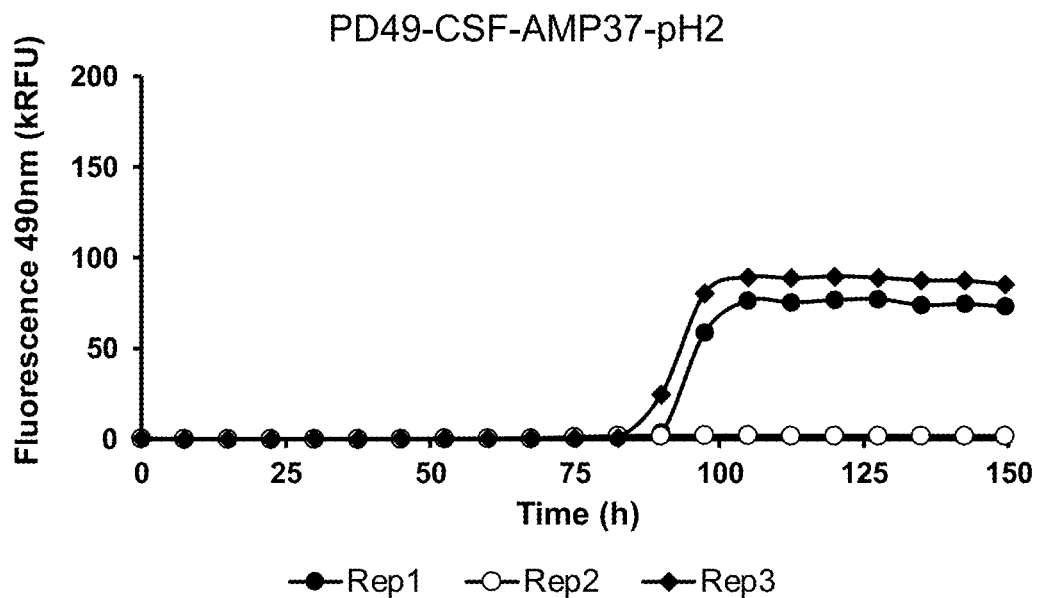
Figure 8B:
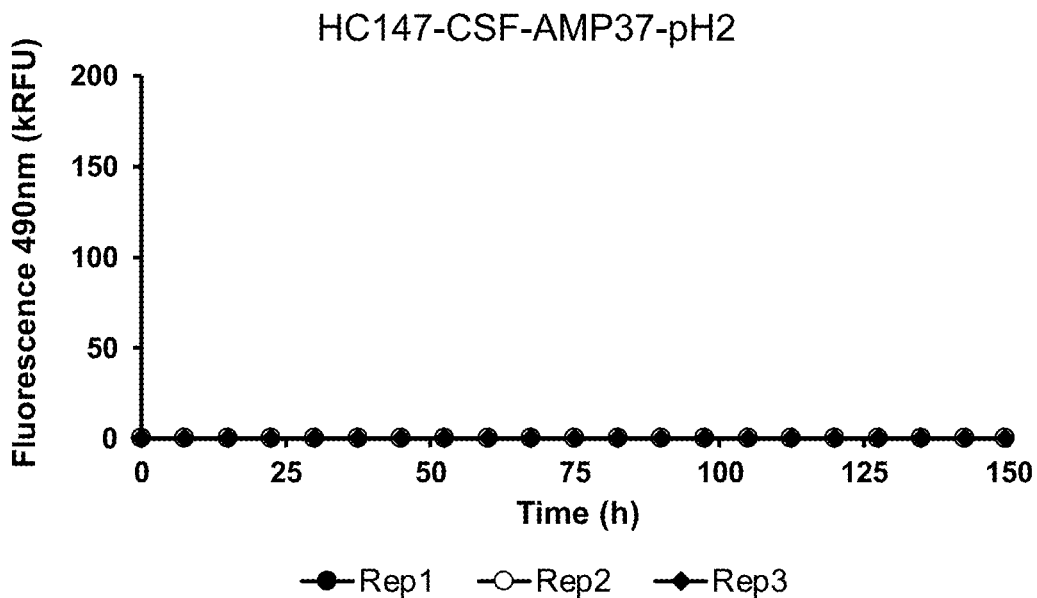

FIG. 8A and FIG. 8B show αS-SAA "fast assay" aggregation curves (of three replicates individually) using the monomeric αS substrate corresponding to SEQ ID NO: 6 expressed in *E. coli* strain BL21(DE3) transformed using the plasmid represented by SEQ ID NO: 2, purified by acid precipitation to pH 2.0, in the presence of a confirmed PD sample (FIG. 8A) and in an HC (FIG. 8B). The results were consistent with pH 2.5, with no self-aggregation in the HC, but low PD aggregation, as only two of the three replicates were positive.

Figure 9A:
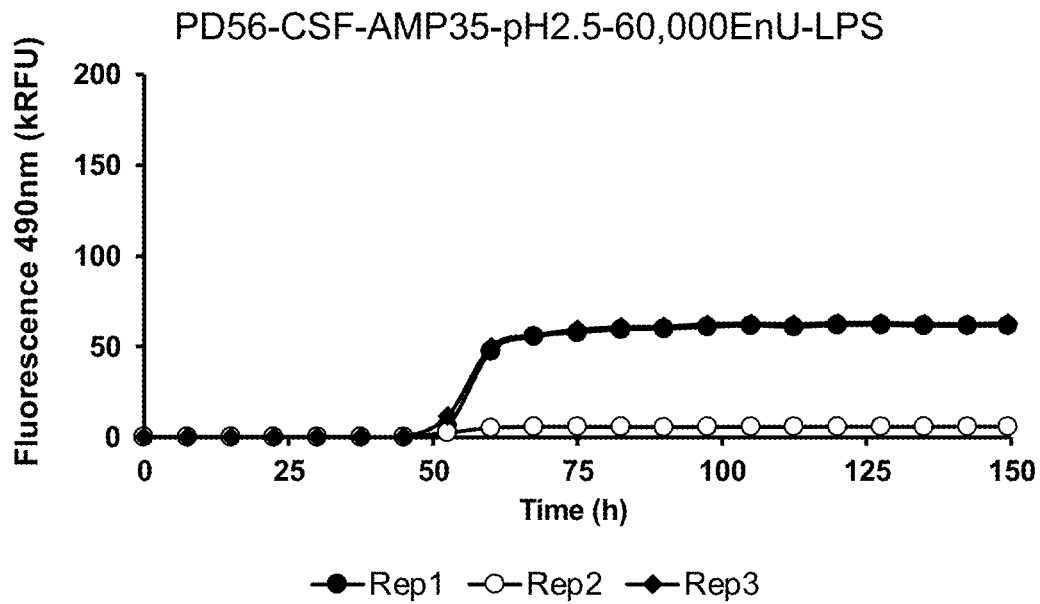
Figure 9B:
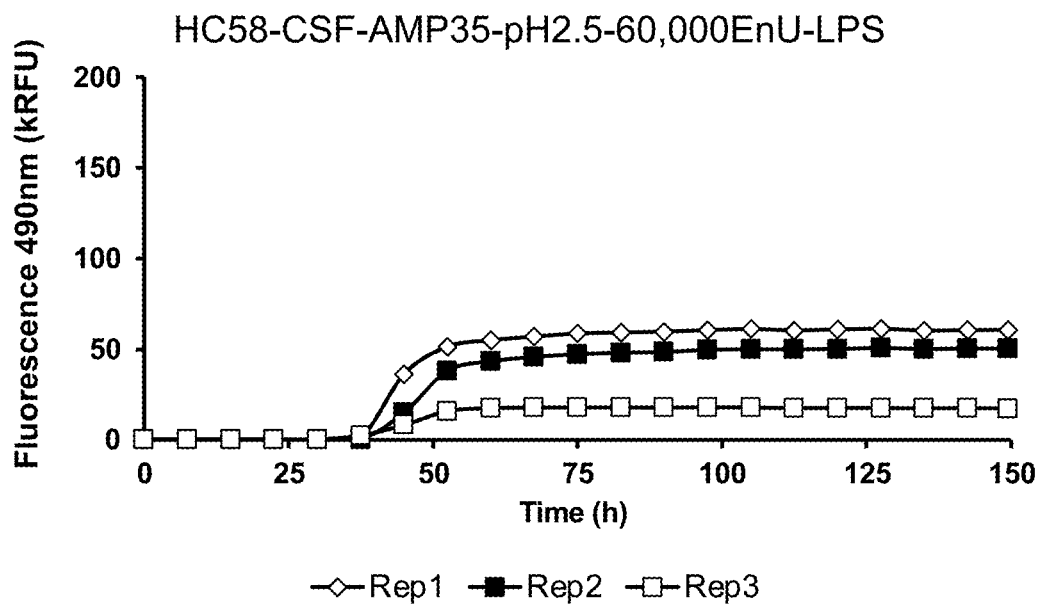
Figure 9C:
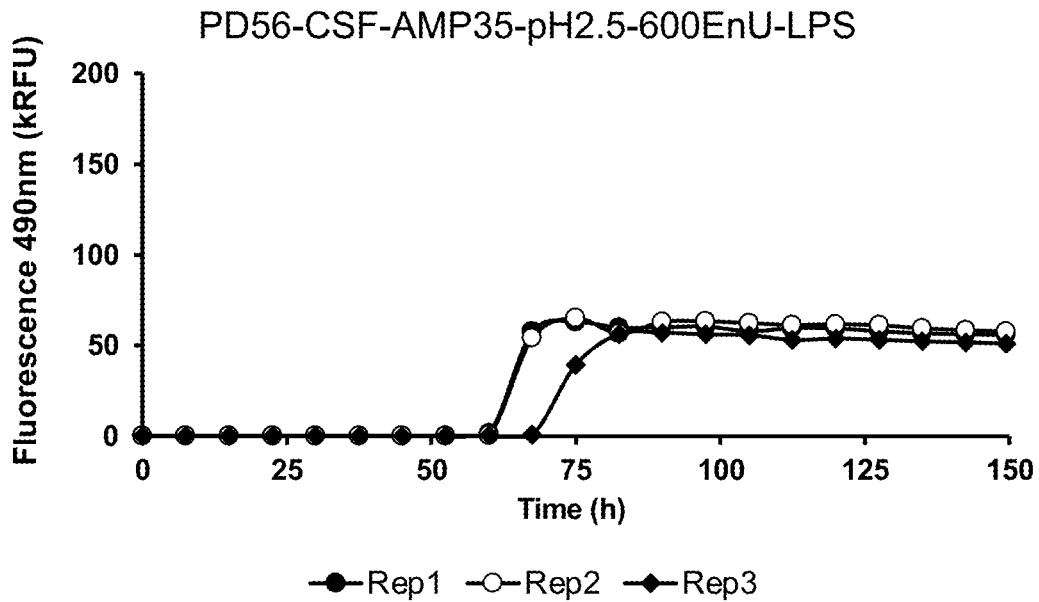
Figure 9D:
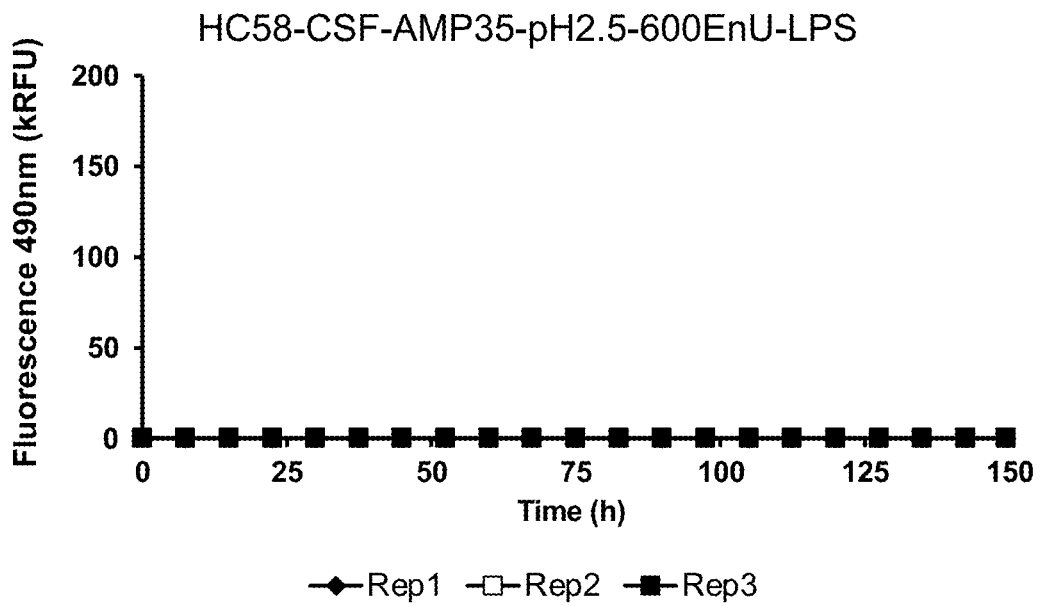

Example 4: Addition of LPS to Acid Precipitated (pH 2.5) Monomeric αS Substrate Prior to αS-SAA of PD Sample LPS was added to the acid precipitated (pH 2.5) monomeric αS substrate described in Example 3. FIG. 9A shows αS-SAA "fast assay" aggregation curves (of three replicates individually) in the presence of a confirmed PD sample using 60,000 Endotoxin Units (EnU) of LPS. The LPS accelerated the aggregation, which started around 50 hours. Two of the replicates were clearly positive and showed reproducible aggregation, while the third one displayed a much lower maximum fluorescence (Fmax). Despite the variability and low Fmax of one replicate, this sample would be considered positive. 60,000 EnU of LPS induced very high levels of self-aggregation (FIG. 9B). An LPS addition of 600 EnU substantially improved the reproducibility of the three replicates, which were all positive at the expected 50-75 hours (FIG. 9C). Strikingly, 600 EnU of LPD did not induce self-aggregation, allowing clear identification of the HC sample as negative (FIG. 9D).

Figure 10A:
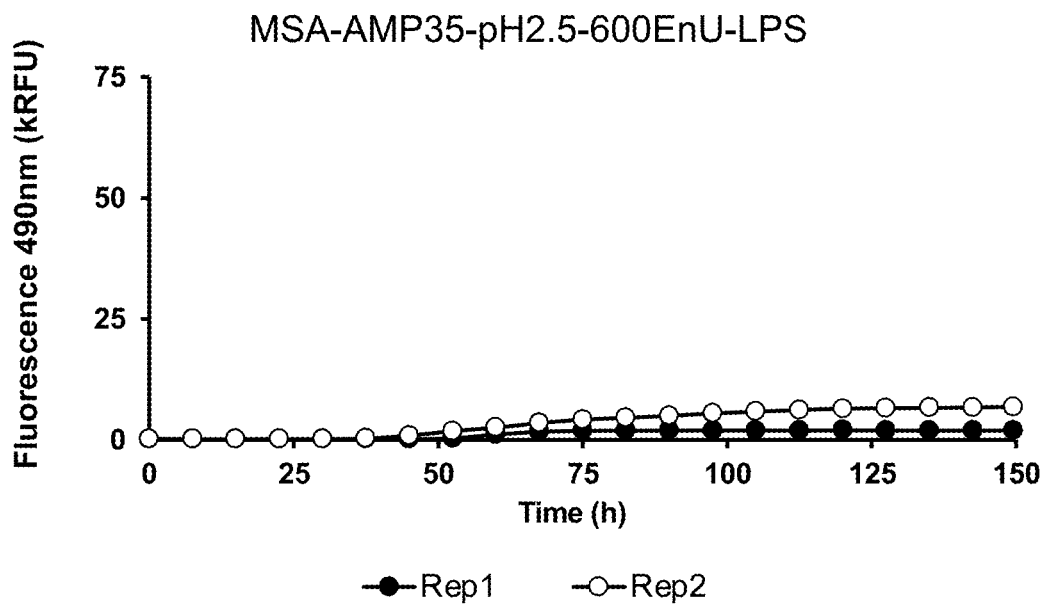
FIG. 10A and FIG. 10B show αS-SAA "fast assay" aggregation curves (of two replicates individually) using the monomeric αS substrate corresponding to SEQ ID NO: 6 expressed in *E. coli* strain BL21(DE3) transformed using the plasmid represented by SEQ ID NO: 2, purified by acid precipitation to pH 2.5 and further supplemented with varying amounts of LPS, in the presence of confirmed MSA samples.
Figure 10B:
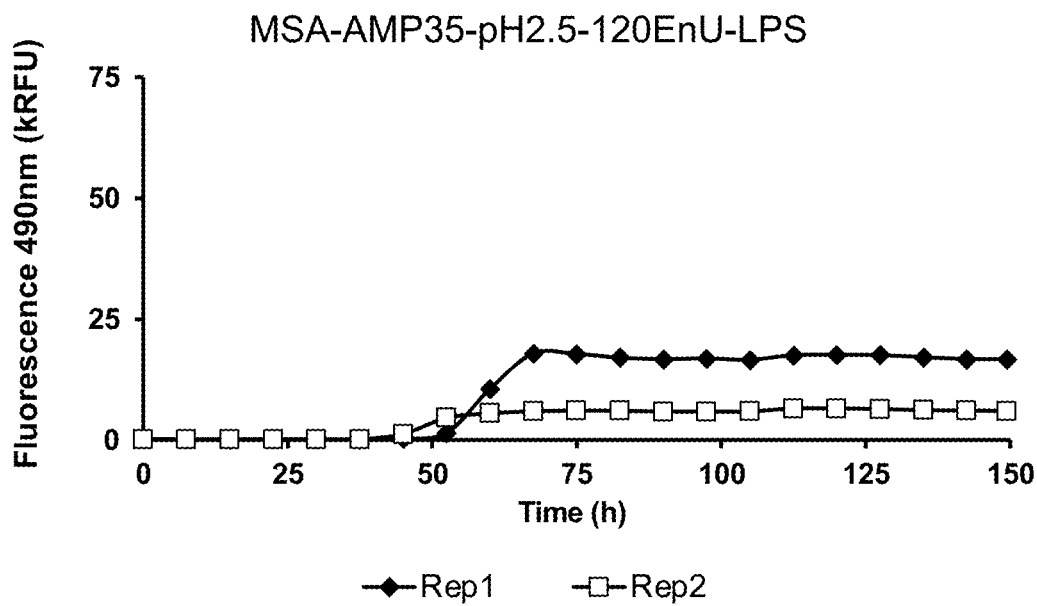

Example 5: Addition of LPS to Acid Precipitated (pH 2.5) Monomeric αS Substrate Prior to αS-SAA of MSA Sample LPS was added to the acid precipitated (pH 2.5) monomeric αS substrate. FIG. 10A and FIG. 10B show αS-SAA "fast assay" aggregation curves (of two replicates individually) in the presence of a confirmed MSA sample using 600 EnU and 120 EnU, respectively. The LPS induced aggregation with low fluorescence, consistent with MSA diagnosis.

Example 5: Purification of αS Protein by Microfluidization and Double Acid Precipitation FIG. 11 shows a flowchart of an example method for purifying monomeric αS substrate that, together with proper αS-SAA conditions, reduces, slows, or prevents altogether misfolding and self-aggregation when used in an αS-SAA, yet retains its activity in the presence of soluble, misfolded αS protein in a biological sample.

Thus, the bacterial pellets containing αS protein were prepared as described in Example 1, washed, frozen at −80° C., and stored until use. For purification, the cells were thawed in a water bath set to 30° C. for 40-45 min in lysis buffer (50 mM NaH2PO4 pH: 8.0, 0.3M NaCl, 0.2 mM EDTA, 20 mM Imidazole, 1 mM PMSF, 0.1 mM TCEP). The cells were resuspended in a final volume of lysis buffer equivalent to 4× the weight of the pellet (80 mL lysis buffer to 20 g of pellet). The resuspended cells were degassed using a standard vacuum pump. The resuspended cells were lysed by a microfluidizer (LM20 Microfluidizer made by Microfluidics™). The crude lysate was clarified by centrifugation to remove large cellular debris.

The clarified lysate was titrated by stepwise addition of 1M HCl during agitation. After reaching a target pH of 3.5, the acidified lysate was incubated with agitation for 20-60 min. The acidified lysate was clarified by centrifugation. The clarified lysate was again titrated by stepwise addition of 1M HCl during agitation. After reaching a target pH of 2.0, the acidified lysate was incubated with agitation for 20-60 min. The double acidified lysate was clarified by centrifugation, filtered by 0.45 μm filters, and the supernatant was neutralized using 1M NaOH to pH 8.00. The neutralized lysate was filtered by 0.22 μm filters, and the material was loaded onto a column with nickel-Sepharose resin.

Chromatography was carried out using standard protocols. After loading the neutralized filtered lysate, the packed column was washed with a first wash buffer (50 mM NaH2PO4 pH: 7.4, 0.5M NaCl, 20 mM Imidazole, 0.1 mM TCEP) and a second wash buffer (50 mM NaH2PO4 pH: 7.4, 0.15M NaCl, 20 mM Imidazole, 0.1 mM TCEP). Protein was eluted with elution buffer (50 mM NaH2PO4 pH: 7.4, 0.15M NaCl, 250 mM Imidazole, 0.1 mM TCEP), and elution fractions were collected on ice. The elution fractions were evaluated by SDS-PAGE and Coomassie staining to determine the fractions with the lower amounts of contaminants and higher amounts of recombinant αS protein.

After pooling the elution fractions with high αS and low contaminants, the pool was dialyzed for 4-5 h in 1×PBS at a dilution factor of 1:200. A second dialysis was performed (1:400) overnight for a total 1:80,000 dilution factor.

The dialyzed material was filtered using a 50,000 Dalton MWCO Amicon centrifugal device. The 50 kDa filtered material is the final αS monomer product and protein concentration was determined by BCA, A280, or a combination of A280 and BCA for increased accuracy. The protein was aliquoted into single use aliquots containing around 6.5 mg each.

FIGS. 12A-12D show αS-SAA "fast assay" aggregation curves (of three replicates individually) of the resultant αS protein in the presence of three different confirmed PD samples (FIGS. 12A-12C) and in an HC (FIG. 12D). The PD samples showed excellent reproducibility, and the HC showed no self-aggregation. This is surprising and counter-intuitive in view of the self-aggregation exhibited in the HC using a single acid precipitation step at pH 3.5 (FIG. 5B) and the lack of desired aggregation in the PD sample using a single acid precipitation step at pH 2.0 (FIG. 8A).

Example 6: Purification of αS Protein by Microfluidization, Acid Precipitation, and Multiple Filtration The αS substrate was prepared as described in Example 2, with the acid precipitation pH target at about 3.1, except that one aliquot of the dialyzed, filtered αS substrate was filtered a second time at 50 kDa and one aliquot of the dialyzed, filtered αS substrate was filtered a second time at 30 kDa.

FIGS. 13A-13D show αS-SAA "fast assay" aggregation curves (of three replicates individually) using the monomeric αS substrate corresponding to SEQ ID NO: 6 expressed in E. coli strain BL21(DE3) transformed using the plasmid represented by SEQ ID NO: 2, purified by acid precipitation to pH about 3.1, and further purified by a second filtration of the dialyzed, filtered protein using a 50 kDa filter in the presence of synthetic seeds (FIG. 13A) and in an HC (FIG. 13B) or using a 30 kDa filter in the presence of synthetic seeds (FIG. 13C) and in an HC (FIG. 13D).

Unless defined otherwise, all technical and scientific terms used herein have the same meaning as commonly understood by one of ordinary skill in the art to which this invention belongs.

Where a range of values is provided, each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

The term "about" in conjunction with a number is intended to include ±10% of the number. This is true whether "about" is modifying a stand-alone number or modifying a number at either or both ends of a range of numbers. In other words, "about 10" means from 9 to 11. Likewise, "about 10 to about 20" contemplates 9 to 22 and 11 to 18. In the absence of the term "about," the exact number is intended. In other words, "10" means 10.

The singular forms "a", "and", and "the" include plural referents unless the context clearly dictates otherwise. Thus, for example, reference to "a sample" also includes a plurality of such samples and reference to "a monomeric αS substrate" includes reference to one or more such molecule, and so forth.

The complete disclosure of all patents, patent applications, and publications, and electronically available material cited herein are incorporated by reference, whether or not the specific citation herein so states. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An expression vector for production of a protein comprising SEQ ID NO: 6, the expression vector comprising:
   a nucleic acid sequence coding for SEQ ID NO: 6 comprising codons that have been optimized to produce SEQ ID NO: 6 when expressed by an enterobacterial host cell, wherein the nucleic acid sequence comprises a sequence having at least 95% identity with SEQ ID NO: 1 wherein the protein has alpha-synuclein activity.

2. The expression vector of claim 1, further comprising a nucleic acid sequence having at least 95% identity with SEQ ID NO: 2.

3. A method for preparing a protein comprising SEQ ID NO: 6, the method comprising:
  transforming into an enterobacterial host cell an expression vector comprising a nucleic acid sequence coding for SEQ ID NO: 6 comprising codons that have been optimized to produce SEQ ID NO: 6 when expressed by the enterobacterial host cell, wherein the nucleic acid sequence comprises a sequence having at least 95% identity with SEQ ID NO: 1;
  culturing the enterobacterial host cell under conditions effective to produce the protein; and
  obtaining the protein from the enterobacterial host cell.

4. The method of claim 3, wherein the expression vector further comprises a nucleic acid sequence having at least 95% identity with SEQ ID NO: 2.

5. The method of claim 3, wherein the enterobacteria comprises *Escherichia coli*.

6. The method of claim 3, wherein the obtaining comprises lysing the transformed cell using a microfluidizer.

7. The method of claim 6, wherein the lysing produces a cell lysate, and the method further comprises:
  (i) clarifying the cell lysate; and
  (ii) contacting the clarified lysate with a synthetic adsorbent of crystalline calcium silicate hydrate.

8. The method of claim 6, wherein the lysing produces a cell lysate, and the method further comprises:
  (i) clarifying the cell lysate; and
  (ii) titrating the clarified lysate with acid to a pH of about 3.5 or less.

9. The method of claim 6, wherein the lysing produces a cell lysate, and the method further comprises:
  (i) clarifying the cell lysate;
  (ii) titrating the clarified lysate with acid to a pH of about 2 or less; and
  (iii) adding lipopolysaccharide.

10. The method of claim 9, further comprising, prior to adding the lipopolysaccharide:
  (i) neutralizing the acidified lysate;
  (ii) filtering the neutralized lysate;
  (iii) subjecting the filtered lysate to chromatography to yield the protein;
  (iv) filtering the protein;
  (v) dialyzing the filtered protein; and
  (vi) filtering the dialyzed protein.

11. The method of claim 10, further comprising filtering the dialyzed, filtered protein at least a second time.

12. The method of claim 6, wherein the lysing produces a cell lysate, and the method further comprises:
  (i) clarifying the cell lysate;
  (ii) titrating the clarified lysate with acid to a pH of about 3.5 to produce a first acidified lysate;
  (iii) clarifying the first acidified lysate; and
  (iv) acidifying the clarified, first acidified lysate to a pH of less than about 2 to produce a second acidified lysate.

13. The method of claim 12, further comprising:
  (i) clarifying the second acidified lysate;
  (ii) filtering the second acidified lysate;
  (iii) neutralizing the filtered, second acidified lysate;
  (iv) filtering the neutralized lysate;
  (v) subjecting the filtered, neutralized lysate to chromatography to yield the protein;
  (vi) filtering the protein;
  (vii) dialyzing the filtered protein; and
  (viii) filtering the dialyzed protein.

* * * * *

SEQUENCE LISTING

<160> NUMBER OF SEQ ID NOS: 23

<210> SEQ ID NO 1
<211> LENGTH: 441
<212> TYPE: DNA
<213> ORGANISM: Artificial Sequence
<220> FEATURE:
<223> OTHER INFORMATION: Synthetic

<400> SEQUENCE: 1

```
atggacgtgt ttatgaaagg tctgtctaaa gcgaaggaag gtgttgtggc ggctgcggag        60
aaaacgaaac agggtgtcgc agaggctgca ggcaagacga aagagggcgt cttgtacgtg       120
ggtagcaaga ccaaagaggg tgtcgtgcac ggtgtcgcga ccgttgccga aaagactaaa       180
gaacaagtca ccaatgttgg tggcgcagtt gtgaccggtg ttaccgccgt cgcgcaaaag       240
accgttgagg gtgcgggcag cattgcggca gcgacgggtt tcgtgaaaaa agatcaactg       300
ggtaagaacg aagagggcgc tccacaggaa ggcatcctgg aagatatgcc ggttgatccg       360
gacaacgaag cctacgaaat gccgagcgaa gagggctatc aggactatga gcctgaggca       420
caccaccatc atcatcacta a                                                441
```

<210> SEQ ID NO 2

<211> LENGTH: 4398
<212> TYPE: DNA
<213> ORGANISM: Artificial Sequence
<220> FEATURE:
<223> OTHER INFORMATION: Synthetic

<400> SEQUENCE: 2

| | | | | | |
|---|---|---|---|---|---|
| cccgtagaaa | agatcaaagg | atcttcttga | gatccttttt | ttctgcgcgt | aatctgctgc | 60 |
| ttgcaaacaa | aaaaccacc | gctaccagcg | gtggtttgtt | tgccggatca | agagctacca | 120 |
| actctttttc | cgaaggtaac | tggcttcagc | agagcgcaga | taccaaatac | tgttcttcta | 180 |
| gtgtagccgt | agttagccca | ccacttcaag | aactctgtag | caccgcctac | atacctcgct | 240 |
| ctgctaatcc | tgttaccagt | ggctgctgcc | agtggcgata | agtcgtgtct | taccgggttg | 300 |
| gactcaagac | gatagttacc | ggataaggcg | cagcggtcgg | gctgaacggg | gggttcgtgc | 360 |
| acacagccca | gcttggagcg | aacgacctac | accgaactga | gatacctaca | gcgtgagcta | 420 |
| tgagaaagcg | ccacgcttcc | cgaagggaga | aaggcggaca | ggtatccggt | aagcggcagg | 480 |
| gtcggaacag | gagagcgcac | gagggagctt | ccaggggaa | acgcctggta | tctttatagt | 540 |
| cctgtcgggt | ttcgccacct | ctgacttgag | cgtcgatttt | tgtgatgctc | gtcaggggg | 600 |
| cggagcctat | ggaaaaacgc | cagcaacgcg | gcctttttac | ggttcctggc | cttttgctgg | 660 |
| ccttttgctc | acatgttctt | tcctgcgtta | tcccctgatt | ctgtggataa | ccgtattacc | 720 |
| gcctttgagt | gagctgatac | cgctcgccgc | agccgaacga | ccgagcgcag | cgagtcagtg | 780 |
| agcgaggaag | cggaaggcga | gagtagggaa | ctgccaggca | tcaaactaag | cagaaggccc | 840 |
| ctgacgatg | gccttttgc | gtttctacaa | actcttctg | tgttgtaaaa | cgacggccag | 900 |
| tcttaagctc | gggccccctg | ggcggttctg | ataacgagta | atcgttaatc | cgcaaataac | 960 |
| gtaaaaaccc | gcttcggcgg | gtttttttat | ggggggagt | tagggaaaga | gcatttgtca | 1020 |
| gaatatttaa | gggcgcctgt | cactttgctt | gatatatgag | aattatttaa | ccttataaat | 1080 |
| gagaaaaag | caacgcactt | taaataagat | acgttgcttt | tcgattgat | gaacaccctat | 1140 |
| aattaaacta | ttcatctatt | atttatgatt | ttttgtatat | acaatatttc | tagtttgtta | 1200 |
| aagagaatta | agaaaataaa | tctcgaaaat | aataaaggga | aaatcagttt | ttgatatcaa | 1260 |
| aattatacat | gtcaacgata | atacaaaata | taatacaaac | tataagatgt | tatcagtatt | 1320 |
| tattatgcat | ttagaataaa | ttttgtgtcg | cccttccgcg | aaattaatac | gactcactat | 1380 |
| agggaattg | tgagcggata | acaattcccc | tctagaaata | attttgttta | actttttgag | 1440 |
| accttaagga | ggtaaaaaat | ggacgtgttt | atgaaaggtc | tgtctaaagc | gaaggaaggt | 1500 |
| gttgtggcgg | ctgcggagaa | aacgaaacag | ggtgtcgcag | aggctgcagg | caagacgaaa | 1560 |
| gagggcgtct | tgtacgtggg | tagcaagacc | aaagagggtg | tcgtcacgg | tgtcgcgacc | 1620 |
| gttgccgaaa | agactaaaga | acaagtcacc | aatgttggtg | gcgcagttgt | gaccggtgtt | 1680 |
| accgccgtcg | cgcaaaagac | cgttgagggt | gcgggcagca | ttgcggcagc | gacgggtttc | 1740 |
| gtgaaaaaag | atcaactggg | taagaacgaa | gagggcgctc | cacaggaagg | catcctggaa | 1800 |
| gatatgccgg | ttgatccgga | caacgaagcc | tacgaaatgc | cgagcgaaga | gggctatcag | 1860 |
| gactatgagc | ctgaggcaca | ccaccatcat | catcactaag | gttgaggtct | cacccccctag | 1920 |
| cataaccct | tggggcctct | aaacgggtct | tgagggtt | tttgcccctg | agacgcgtca | 1980 |
| atcgagttcg | tacctaaggg | cgacacccc | taattagccc | gggcgaaagg | cccagtctt | 2040 |
| cgactgagcc | tttcgtttta | tttgatgcct | ggcagttccc | tactctcgca | tggggagtcc | 2100 |
| ccacactacc | atcggcgcta | cggcgtttca | cttctgagtt | cggcatgggg | tcaggtggga | 2160 |

```
ccaccgcgct actgccgcca ggcaaacaag gggtgttatg agccatattc aggtataaat      2220
gggctcgcga taatgttcag aattggttaa ttggttgtaa cactgacccc tatttgttta      2280
tttttctaaa tacattcaaa tatgtatccg ctcatgagac aataaccctg ataaatgctt      2340
caataatatt gaaaaggaa gaatatgagc catattcaac gggaaacgtc gaggccgcga       2400
ttaaattcca acatggatgc tgatttatat gggtataaat gggctcgcga taatgtcggg      2460
caatcaggtg cgacaatcta tcgcttgtat gggaagcccg atgcgccaga gttgtttctg      2520
aaacatggca aaggtagcgt tgccaatgat gttacagatg agatggtcag actaaactgg      2580
ctgacggaat ttatgccact tccgaccatc aagcatttta tccgtactcc tgatgatgca      2640
tggttactca ccactgcgat ccccggaaaa acagcgttcc aggtattaga agaatatcct      2700
gattcaggtg aaaatattgt tgatgcgctg gcagtgttcc tgcgccggtt gcactcgatt      2760
cctgtttgta attgtccttt taacagcgat cgcgtatttc gcctcgctca ggcgcaatca      2820
cgaatgaata acggtttggt tgatgcgagt gattttgatg acgagcgtaa tggctggcct      2880
gttgaacaag tctggaaaga atgcataaa cttttgccat tctcaccgga ttcagtcgtc       2940
actcatggtg atttctcact tgataaacctt attttttgacg aggggaaatt aataggttgt    3000
attgatgttg gacgagtcgg aatcgcagac cgataccagg atcttgccat cctatggaac     3060
tgcctcggtg agttttctcc ttcattacag aaacggcttt ttcaaaaata tggtattgat      3120
aatcctgata tgaataaatt gcagtttcat ttgatgctcg atgagttttt ctaagcggcg     3180
cgccatcgaa tggcgcaaaa cctttcgcgg tatggcatga tagcgcccgg aagagagtca     3240
attcagggtg gtgaatatga aaccagtaac gttatacgat gtcgcagagt atgccggtgt     3300
ctcttatcag accgtttccc gcgtggtgaa ccaggccagc cacgtttctg cgaaaacgcg     3360
ggaaaaagtg gaagcggcga tggcggagct gaattacatt cccaaccgcg tggcacaaca     3420
actggcgggc aaacagtcgt tgctgattgg cgttgccacc tccagtctgg ccctgcacgc     3480
gccgtcgcaa attgtcgcgg cgattaaatc tcgcgccgat caactgggtg ccagcgtggt    3540
ggtgtcgatg gtagaacgaa gcggcgtcga agcctgtaaa gcggcggtgc acaatcttct     3600
cgcgcaacgc gtcagtgggc tgatcattaa ctatccgctg gatgaccagg atgccattgc     3660
tgtggaagct gcctgcacta atgttccggc gttatttctt gatgtctctg accagacacc     3720
catcaacagt attatttct cccatgagga cggtacgcga ctgggcgtgg agcatctggt     3780
cgcattgggt caccagcaaa tcgcgctgtt agcgggccca ttaagttctg tctcggcgcg     3840
tctgcgtctg gctggctggc ataaatatct cactcgcaat caaattcagc cgatagcgga     3900
acgggaaggc gactggagtg ccatgtccgg ttttcaacaa accatgcaaa tgctgaatga     3960
gggcatcgtt cccactgcga tgctggttgc caacgatcag atggcgctgg gcgcaatgcg    4020
cgccattacc gagtccgggc tgcgcgttgg tgcggatatc tcggtagtgg gatacgacga     4080
taccgaagat agctcatgtt atatcccgcc gttaaccacc atcaaacagg attttcgcct     4140 gctgggcaa accagcgtgg accgcttgct gcaactctct cagggccagg cggtgaaggg     4200
caatcagctg ttgccagtct cactggtgaa agaaaaaacc accctggcgc ccaatacgca     4260
aaccgcctct ccccgcgcgt tggccgattc attaatgcag ctggcacgac aggtttcccg     4320
actggaaagc gggcagtgac tcatgaccaa aatcccttaa cgtgagttac gcgcgcgtcg     4380
ttccactgag cgtcagac                                                   4398

<210> SEQ ID NO 3
```

```
<211> LENGTH: 441
<212> TYPE: DNA
<213> ORGANISM: Artificial Sequence
<220> FEATURE:
<223> OTHER INFORMATION: Synthetic

<400> SEQUENCE: 3
atggatgtat tcatgaaagg actttcaaag gccaaggagg gagttgtggc tgctgctgag      60
aaaaccaaac agggtgtggc agaagcagca ggaaagacaa aagagggtgt tctctatgta     120
ggctccaaaa ccaaggaggg agtggtgcat ggtgtggcaa cagtggctga aagaccaaa      180 gagcaagtga caaatgttgg aggagcagtg gtgacgggtg tgacagcagt agcccagaag     240
acagtggagg gagcagggag cattgcagca gccactggct ttgtcaaaaa ggaccagttg     300
ggcaagaatg aagaaggagc cccacaggaa ggaattctgg aagatatgcc tgtggatcct     360
gacaatgagg cttatgaaat gccttctgag aagggtatc aagactacga acctgaagcc      420
catcatcacc accatcacta a                                              441

<210> SEQ ID NO 4
<211> LENGTH: 4398
<212> TYPE: DNA
<213> ORGANISM: Artificial Sequence
<220> FEATURE:
<223> OTHER INFORMATION: Synthetic

<400> SEQUENCE: 4
cccgtagaaa agatcaaagg atcttcttga gatccttttt ttctgcgcgt aatctgctgc      60
ttgcaaacaa aaaaccacc gctaccagcg gtggtttgtt tgccggatca agagctacca      120
actctttttc cgaaggtaac tggcttcagc agagcgcaga taccaaatac tgttcttcta     180
gtgtagccgt agttagccca ccacttcaag aactctgtag caccgcctac atacctcgct     240
ctgctaatcc tgttaccagt ggctgctgcc agtggcgata agtcgtgtct taccgggttg     300
gactcaagac gatagttacc ggataaggcg cagcggtcgg gctgaacggg gggttcgtgc     360
acacagccca gcttggagcg aacgacctac accgaactga gatacctaca gcgtgagcta     420
tgagaaagcg ccacgcttcc cgaagggaga aaggcggaca ggtatccggt aagcggcagg     480
gtcggaacag gagagcgcac gagggagctt ccaggggaa acgcctggta tctttatagt      540
cctgtcgggt ttcgccacct ctgacttgag cgtcgatttt tgtgatgctc gtcaggggg      600 cggagcctat ggaaaaacgc cagcaacgcg gcctttttac ggttcctggc cttttgctgg     660
ccttttgctc acatgttctt tcctgcgtta tcccctgatt ctgtggataa ccgtattacc     720
gcctttgagt gagctgatac cgctcgccgc agccgaacga ccgagcgcag cgagtcagtg     780
agcgaggaag cggaaggcga gagtagggaa ctgccaggca tcaaactaag cagaaggccc     840
ctgacggatg cctttttgc gtttctacaa actctttctg tgttgtaaaa cgacggccag      900
tcttaagctc gggcccctg gcggttctg ataacgagta atcgttaatc cgcaaataac       960
gtaaaaaccc gcttcggcgg gtttttttat gggggggagtt tagggaaaga gcatttgtca    1020
gaatatttaa gggcgcctgt cactttgctt gatatatgag aattatttaa ccttataaat    1080
gagaaaaaag caacgcactt taaataagat acgttgcttt tcgattgat gaacaccta      1140 aattaaacta ttcatctatt atttatgatt ttttgtatat acaatatttc tagttgtta     1200 aagagaatta agaaaataaa tctcgaaaat aataagggaa aaatcagttt tgatatcaa     1260 aattatacat gtcaacgata atacaaata taatacaaac tataagatgt tatcagtatt    1320
tattatgcat ttagaataaa ttttgtgtcg cccttccgcg aaattaatac gactcactat    1380
```

```
aggggaattg tgagcggata acaattcccc tctagaaata attttgttta acttttgag    1440 accttaagga ggtaaaaaat ggatgtattc atgaaaggac tttcaaaggc caaggaggga    1500
gttgtggctg ctgctgagaa aaccaaacag ggtgtggcag aagcagcagg aaagacaaaa    1560
gagggtgttc tctatgtagg ctccaaaacc aaggaggag tggtgcatgg tgtggcaaca     1620
gtggctgaga agaccaaaga gcaagtgaca aatgttggag gagcagtggt gacgggtgtg    1680
acagcagtag cccagaagac agtggaggga gcagggagca ttgcagcagc cactggcttt    1740
gtcaaaaagg accagttggg caagaatgaa gaaggagccc cacaggaagg aattctggaa    1800
gatatgcctg tggatcctga caatgaggct tatgaaatgc cttctgagga agggtatcaa    1860
gactacgaac ctgaagccca tcatcaccac catcactaag gttgaggtct cacccctag    1920 cataacccct tggggcctct aaacgggtct tgagggggttt tttgcccctg agacgcgtca    1980
atcgagttcg tacctaaggg cgacaccccc taattagccc gggcgaaagg cccagtcttt    2040
cgactgagcc tttcgtttta tttgatgcct ggcagttccc tactctcgca tggggagtcc    2100
ccacactacc atcggcgcta cggcgtttca cttctgagtt cggcatgggg tcaggtggga    2160
ccaccgcgct actgccgcca ggcaaacaag gggtgttatg agccatattc aggtataaat    2220
gggctcgcga taatgttcag aattggttaa ttggttgtaa cactgacccc tatttgttta    2280
tttttctaaa tacattcaaa tatgtatccg ctcatgagac aataaccctg ataaatgctt    2340
caataatatt gaaaaggaa gaatatgagc catattcaac gggaaacgtc gaggccgcga     2400
ttaaattcca acatggatgc tgatttatat gggtataaat gggctcgcga taatgtcggg    2460
caatcaggtg cgacaatcta tcgcttgtat gggaagcccg atgcgccaga gttgtttctg    2520
aaacatggca aaggtagcgt tgccaatgat gttacagatg agatggtcag actaaactgg    2580
ctgacggaat ttatgccact tccgaccatc aagcatttta tccgtactcc tgatgatgca    2640
tggttactca ccactgcgat ccccggaaaa acagcgttcc aggtattaga agaatatcct    2700
gattcaggtg aaaatattgt tgatgcgctg gcagtgttcc tgcgccggtt gcactcgatt    2760
cctgtttgta attgtccttt taacagcgat cgcgtatttc gcctcgctca ggcgcaatca    2820
cgaatgaata acggtttggt tgatgcgagt gattttgatg acgagcgtaa tggctggcct    2880
gttgaacaag tctggaaaga atgcataaa cttttgccat tctcaccgga ttcagtcgtc     2940
actcatggtg atttctcact tgataacctt attttttgacg aggggaaatt aataggttgt    3000
attgatgttg gacgagtcgg aatcgcagac cgataccagg atcttgccat cctatggaac    3060
tgcctcggtg agttttctcc ttcattacag aaacggcttt ttcaaaaata tggtattgat    3120
aatcctgata tgaataaatt gcagtttcat ttgatgctcg atgagttttt ctaagcggcg    3180
cgccatcgaa tggcgcaaaa cctttcgcgg tatggcatga tagcgcccgg aagagagtca    3240
attcagggtg gtgaatatga aaccagtaac gttatacgat gtcgcagagt atgccggtgt    3300
ctcttatcag accgtttccc gcgtggtgaa ccaggccagc cacgtttctg cgaaaacgcg    3360
ggaaaaagtg gaagcggcga tggcggagct gaattacatt cccaaccgcg tggcacaaca    3420 actggcggc aaacagtcgt tgctgattgg cgttgccacc tccagtctgg ccctgcacgc     3480
gccgtcgcaa attgtcgcgg cgattaaatc tcgcgccgat caactgggtg ccagcgtggt    3540
ggtgtcgatg gtagaacgaa gcggcgtcga agcctgtaaa gcggcggtgc acaatcttct    3600
cgcgcaacgc gtcagtgggc tgatcattaa ctatccgctg gatgaccagg atgccattgc    3660
tgtggaagct gcctgcacta atgttccggc gttatttctt gatgtctctg accagacacc    3720
```

```
catcaacagt attattttct cccatgagga cggtacgcga ctgggcgtgg agcatctggt   3780
cgcattgggt caccagcaaa tcgcgctgtt agcgggccca ttaagttctg tctcggcgcg   3840
tctgcgtctg gctggctggc ataaatatct cactcgcaat caaattcagc cgatagcgga   3900
acgggaaggc gactggagtg ccatgtccgg ttttcaacaa accatgcaaa tgctgaatga   3960
gggcatcgtt cccactgcga tgctggttgc caacgatcag atggcgctgg cgcaatgcg   4020 cgccattacc gagtccgggc tgcgcgttgg tgcggatatc tcggtagtgg gatacgacga   4080
taccgaagat agctcatgtt atatcccgcc gttaaccacc atcaaacagg attttcgcct   4140
gctggggcaa accagcgtgg accgcttgct gcaactctct cagggccagg cggtgaaggg   4200
caatcagctg ttgccagtct cactggtgaa aagaaaaacc accctggcgc ccaatacgca   4260
aaccgcctct ccccgcgcgt tggccgattc attaatgcag ctggcacgac aggtttcccg   4320 actgaaagc gggcagtgac tcatgaccaa aatcccttaa cgtgagttac gcgcgcgtcg   4380
ttccactgag cgtcagac                                                 4398
```

<210> SEQ ID NO 5
<211> LENGTH: 140
<212> TYPE: PRT
<213> ORGANISM: Artificial Sequence
<220> FEATURE:
<223> OTHER INFORMATION: Synthetic

<400> SEQUENCE: 5

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
```

<210> SEQ ID NO 6
<211> LENGTH: 146
<212> TYPE: PRT
<213> ORGANISM: Artificial Sequence
<220> FEATURE:
<223> OTHER INFORMATION: Synthetic

<400> SEQUENCE: 6

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45
```

Val His Gly Val Ala Thr Val Ala Glu Lys Thr Lys Glu Gln Val Thr
                50                  55                  60

Asn Val Gly Gly Ala Val Val Thr Gly Val Thr Ala Val Ala Gln Lys
 65                  70                  75                  80

Thr Val Glu Gly Ala Gly Ser Ile Ala Ala Thr Gly Phe Val Lys
                 85                  90                  95

Lys Asp Gln Leu Gly Lys Asn Glu Gly Ala Pro Gln Glu Gly Ile
                100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala His His His His
        130                 135                 140

His His
145

<210> SEQ ID NO 7
<211> LENGTH: 146
<212> TYPE: PRT
<213> ORGANISM: Artificial Sequence
<220> FEATURE:
<223> OTHER INFORMATION: Synthetic

<400> SEQUENCE: 7

His His His His His His Met Asp Val Phe Met Lys Gly Leu Ser Lys
 1               5                  10                  15

Ala Lys Glu Gly Val Val Ala Ala Ala Glu Lys Thr Lys Gln Gly Val
                20                  25                  30

Ala Glu Ala Ala Gly Lys Thr Lys Glu Gly Val Leu Tyr Val Gly Ser
            35                  40                  45

Lys Thr Lys Glu Gly Val Val His Gly Val Ala Thr Val Ala Glu Lys
 50                  55                  60

Thr Lys Glu Gln Val Thr Asn Val Gly Gly Ala Val Val Thr Gly Val
 65                  70                  75                  80

Thr Ala Val Ala Gln Lys Thr Val Glu Gly Ala Gly Ser Ile Ala Ala
                85                  90                  95

Ala Thr Gly Phe Val Lys Lys Asp Gln Leu Gly Lys Asn Glu Gly Gly
            100                 105                 110

Ala Pro Gln Glu Gly Ile Leu Glu Asp Met Pro Val Asp Pro Asp Asn
        115                 120                 125

Glu Ala Tyr Glu Met Pro Ser Glu Glu Gly Tyr Gln Asp Tyr Glu Pro
    130                 135                 140

Glu Ala
145

<210> SEQ ID NO 8
<211> LENGTH: 147
<212> TYPE: PRT
<213> ORGANISM: Artificial Sequence
<220> FEATURE:
<223> OTHER INFORMATION: Synthetic

<400> SEQUENCE: 8

Met Asp Val Phe Met Lys Gly Leu Ser Lys Ala Lys Glu Gly Val Val
 1               5                  10                  15

Ala Ala Ala Glu Lys Thr Lys Gln Gly Val Ala Glu Ala Ala Gly Lys
                20                  25                  30

Thr Lys Glu Gly Val Leu Tyr Val Gly Ser Lys Thr Lys Glu Gly Val

```
                35                  40                  45
Val His Gly Val Ala Thr Val Ala Glu Lys Thr Lys Glu Gln Val Thr
        50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
                85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
                115                 120                 125

Ser Glu Glu Gly Tyr Gln Asp Tyr Glu Pro Glu Ala Asp Tyr Lys Asp
                130                 135                 140

Asp Asp Asp
145

<210> SEQ ID NO 9
<211> LENGTH: 147
<212> TYPE: PRT
<213> ORGANISM: Artificial Sequence
<220> FEATURE:
<223> OTHER INFORMATION: Synthetic

<400> SEQUENCE: 9

Asp Tyr Lys Asp Asp Asp Met Asp Val Phe Met Lys Gly Leu Ser
1               5                   10                  15

Lys Ala Lys Glu Gly Val Val Ala Ala Ala Glu Lys Thr Lys Gln Gly
                20                  25                  30

Val Ala Glu Ala Ala Gly Lys Thr Lys Glu Gly Val Leu Tyr Val Gly
            35                  40                  45

Ser Lys Thr Lys Glu Gly Val His Gly Val Ala Thr Val Ala Glu
        50                  55                  60

Lys Thr Lys Glu Gln Val Thr Asn Val Gly Gly Ala Val Val Thr Gly
65                  70                  75                  80

Val Thr Ala Val Ala Gln Lys Thr Val Glu Gly Ala Gly Ser Ile Ala
                85                  90                  95

Ala Ala Thr Gly Phe Val Lys Lys Asp Gln Leu Gly Lys Asn Glu Glu
                100                 105                 110

Gly Ala Pro Gln Glu Gly Ile Leu Glu Asp Met Pro Val Asp Pro Asp
            115                 120                 125

Asn Glu Ala Tyr Glu Met Pro Ser Glu Glu Gly Tyr Gln Asp Tyr Glu
        130                 135                 140

Pro Glu Ala
145

<210> SEQ ID NO 10
<211> LENGTH: 148
<212> TYPE: PRT
<213> ORGANISM: Artificial Sequence
<220> FEATURE:
<223> OTHER INFORMATION: Synthetic

<400> SEQUENCE: 10

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
                20                  25                  30
```

```
Thr Lys Glu Gly Val Leu Tyr Val Gly Ser Lys Thr Lys Glu Gly Val
             35                  40                  45

Val His Gly Val Ala Thr Val Ala Glu Lys Thr Lys Glu Gln Val Thr
 50                  55                  60

Asn Val Gly Gly Ala Val Val Thr Gly Val Thr Ala Val Ala Gln Lys
 65                  70                  75                  80

Thr Val Glu Gly Ala Gly Ser Ile Ala Ala Ala Thr Gly Phe Val Lys
                 85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala Asp Tyr Lys Asp
        130                 135                 140

Asp Asp Asp Lys
145
```

<210> SEQ ID NO 11
<211> LENGTH: 148
<212> TYPE: PRT
<213> ORGANISM: Artificial Sequence
<220> FEATURE:
<223> OTHER INFORMATION: Synthetic

<400> SEQUENCE: 11

```
Asp Tyr Lys Asp Asp Asp Lys Met Asp Val Phe Met Lys Gly Leu
 1               5                  10                  15

Ser Lys Ala Lys Glu Gly Val Val Ala Ala Glu Lys Thr Lys Gln
            20                  25                  30

Gly Val Ala Glu Ala Ala Gly Lys Thr Lys Glu Gly Val Leu Tyr Val
             35                  40                  45

Gly Ser Lys Thr Lys Glu Gly Val Val His Gly Val Ala Thr Val Ala
 50                  55                  60

Glu Lys Thr Lys Glu Gln Val Thr Asn Val Gly Gly Ala Val Val Thr
 65                  70                  75                  80

Gly Val Thr Ala Val Ala Gln Lys Thr Val Glu Gly Ala Gly Ser Ile
                 85                  90                  95

Ala Ala Ala Thr Gly Phe Val Lys Lys Asp Gln Leu Gly Lys Asn Glu
            100                 105                 110

Glu Gly Ala Pro Gln Glu Gly Ile Leu Glu Asp Met Pro Val Asp Pro
            115                 120                 125

Asp Asn Glu Ala Tyr Glu Met Pro Ser Glu Glu Gly Tyr Gln Asp Tyr
        130                 135                 140

Glu Pro Glu Ala
145
```

<210> SEQ ID NO 12
<211> LENGTH: 147
<212> TYPE: PRT
<213> ORGANISM: Artificial Sequence
<220> FEATURE:
<223> OTHER INFORMATION: Synthetic

<400> SEQUENCE: 12

```
Met Asp Val Phe Met Lys Gly Leu Ser Lys Ala Lys Glu Gly Val Val
 1               5                  10                  15

Ala Ala Ala Glu Lys Thr Lys Gln Gly Val Ala Glu Ala Ala Gly Lys
            20                  25                  30
```

```
Thr Lys Glu Gly Val Leu Tyr Val Gly Ser Lys Thr Lys Glu Gly Val
         35                  40                  45

Val His Gly Val Ala Thr Val Ala Glu Lys Thr Lys Glu Gln Val Thr
 50                  55                  60

Asn Val Gly Gly Ala Val Val Thr Gly Val Thr Ala Val Ala Gln Lys
 65                  70                  75                  80

Thr Val Glu Gly Ala Gly Ser Ile Ala Ala Thr Gly Phe Val Lys
                 85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
                115                 120                 125

Ser Glu Glu Gly Tyr Gln Asp Tyr Glu Pro Glu Ala Asp Tyr Lys Asp
 130                 135                 140

Asp Asp Lys
 145
```

<210> SEQ ID NO 13
<211> LENGTH: 147
<212> TYPE: PRT
<213> ORGANISM: Artificial Sequence
<220> FEATURE:
<223> OTHER INFORMATION: Synthetic

<400> SEQUENCE: 13

```
Asp Tyr Lys Asp Asp Asp Lys Met Asp Val Phe Met Lys Gly Leu Ser
 1               5                  10                  15

Lys Ala Lys Glu Gly Val Val Ala Ala Ala Glu Lys Thr Lys Gln Gly
                 20                  25                  30

Val Ala Glu Ala Ala Gly Lys Thr Lys Glu Gly Val Leu Tyr Val Gly
                 35                  40                  45

Ser Lys Thr Lys Glu Gly Val Val His Gly Val Ala Thr Val Ala Glu
 50                  55                  60

Lys Thr Lys Glu Gln Val Thr Asn Val Gly Gly Ala Val Val Thr Gly
 65                  70                  75                  80

Val Thr Ala Val Ala Gln Lys Thr Val Glu Gly Ala Gly Ser Ile Ala
                 85                  90                  95

Ala Ala Thr Gly Phe Val Lys Lys Asp Gln Leu Gly Lys Asn Glu Glu
                100                 105                 110

Gly Ala Pro Gln Glu Gly Ile Leu Glu Asp Met Pro Val Asp Pro Asp
                115                 120                 125

Asn Glu Ala Tyr Glu Met Pro Ser Glu Glu Gly Tyr Gln Asp Tyr Glu
 130                 135                 140

Pro Glu Ala
 145
```

<210> SEQ ID NO 14
<211> LENGTH: 149
<212> TYPE: PRT
<213> ORGANISM: Artificial Sequence
<220> FEATURE:
<223> OTHER INFORMATION: Synthetic

<400> SEQUENCE: 14

```
Met Asp Val Phe Met Lys Gly Leu Ser Lys Ala Lys Glu Gly Val Val
 1               5                  10                  15

Ala Ala Ala Glu Lys Thr Lys Gln Gly Val Ala Glu Ala Ala Gly Lys
```

```
                20                  25                  30
Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
                85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asn Glu Ala Tyr Glu Met Pro
            115                 120                 125

Ser Glu Glu Gly Tyr Gln Asp Tyr Glu Pro Glu Ala Tyr Pro Tyr Asp
                130                 135                 140

Val Pro Asp Tyr Ala
145

<210> SEQ ID NO 15
<211> LENGTH: 149
<212> TYPE: PRT
<213> ORGANISM: Artificial Sequence
<220> FEATURE:
<223> OTHER INFORMATION: Synthetic

<400> SEQUENCE: 15

Tyr Pro Tyr Asp Val Pro Asp Tyr Ala Met Asp Val Phe Met Lys Gly
1               5                   10                  15

Leu Ser Lys Ala Lys Glu Gly Val Val Ala Ala Ala Glu Lys Thr Lys
            20                  25                  30

Gln Gly Val Ala Glu Ala Ala Gly Lys Thr Lys Glu Gly Val Leu Tyr
        35                  40                  45

Val Gly Ser Lys Thr Lys Glu Gly Val Val His Gly Val Ala Thr Val
    50                  55                  60

Ala Glu Lys Thr Lys Glu Gln Val Thr Asn Val Gly Gly Ala Val Val
65                  70                  75                  80

Thr Gly Val Thr Ala Val Ala Gln Lys Thr Val Glu Gly Ala Gly Ser
                85                  90                  95

Ile Ala Ala Ala Thr Gly Phe Val Lys Lys Asp Gln Leu Gly Lys Asn
                100                 105                 110

Glu Glu Gly Ala Pro Gln Glu Gly Ile Leu Glu Asp Met Pro Val Asp
            115                 120                 125

Pro Asp Asn Glu Ala Tyr Glu Met Pro Ser Glu Glu Gly Tyr Gln Asp
        130                 135                 140

Tyr Glu Pro Glu Ala
145

<210> SEQ ID NO 16
<211> LENGTH: 149
<212> TYPE: PRT
<213> ORGANISM: Artificial Sequence
<220> FEATURE:
<223> OTHER INFORMATION: Synthetic

<400> SEQUENCE: 16

Met Asp Val Phe Met Lys Gly Leu Ser Lys Ala Lys Glu Gly Val Val
1               5                   10                  15
```

```
Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
               100                 105                 110

Leu Glu Asp Met Pro Val Asp Pro Asp Asn Glu Ala Tyr Glu Met Pro
               115                 120                 125

Ser Glu Glu Gly Tyr Gln Asp Tyr Glu Pro Glu Ala Tyr Ala Tyr Asp
               130                 135                 140

Val Pro Asp Tyr Ala
145

<210> SEQ ID NO 17
<211> LENGTH: 149
<212> TYPE: PRT
<213> ORGANISM: Artificial Sequence
<220> FEATURE:
<223> OTHER INFORMATION: Synthetic

<400> SEQUENCE: 17

Tyr Ala Tyr Asp Val Pro Asp Tyr Ala Met Asp Val Phe Met Lys Gly
1               5                   10                  15

Leu Ser Lys Ala Lys Glu Gly Val Val Ala Ala Glu Lys Thr Lys
            20                  25                  30

Gln Gly Val Ala Glu Ala Ala Gly Lys Thr Lys Glu Gly Val Leu Tyr
        35                  40                  45

Val Gly Ser Lys Thr Lys Glu Gly Val Val His Gly Val Ala Thr Val
    50                  55                  60

Ala Glu Lys Thr Lys Glu Gln Val Thr Asn Val Gly Gly Ala Val Val
65                  70                  75                  80

Thr Gly Val Thr Ala Val Ala Gln Lys Thr Val Glu Gly Ala Gly Ser
                85                  90                  95

Ile Ala Ala Ala Thr Gly Phe Val Lys Lys Asp Gln Leu Gly Lys Asn
               100                 105                 110

Glu Glu Gly Ala Pro Gln Glu Gly Ile Leu Glu Asp Met Pro Val Asp
               115                 120                 125

Pro Asp Asn Glu Ala Tyr Glu Met Pro Ser Glu Glu Gly Tyr Gln Asp
               130                 135                 140

Tyr Glu Pro Glu Ala
145

<210> SEQ ID NO 18
<211> LENGTH: 149
<212> TYPE: PRT
<213> ORGANISM: Artificial Sequence
<220> FEATURE:
<223> OTHER INFORMATION: Synthetic

<400> SEQUENCE: 18

Met Asp Val Phe Met Lys Gly Leu Ser Lys Ala Lys Glu Gly Val Val
1               5                   10                  15
```

```
Ala Ala Ala Glu Lys Thr Lys Gln Gly Val Ala Glu Ala Ala Gly Lys
            20                  25                  30
Thr Lys Glu Gly Val Leu Tyr Val Gly Ser Lys Thr Lys Glu Gly Val
        35                  40                  45
Val His Gly Val Ala Thr Val Ala Glu Lys Thr Lys Glu Gln Val Thr
    50                  55                  60
Asn Val Gly Gly Ala Val Val Thr Gly Val Thr Ala Val Ala Gln Lys
65                  70                  75                  80
Thr Val Glu Gly Ala Gly Ser Ile Ala Ala Thr Gly Phe Val Lys
                85                  90                  95
Lys Asp Gln Leu Gly Lys Asn Glu Glu Gly Ala Pro Gln Glu Gly Ile
                100                 105                 110
Leu Glu Asp Met Pro Val Asp Pro Asp Asn Glu Ala Tyr Glu Met Pro
            115                 120                 125
Ser Glu Glu Gly Tyr Gln Asp Tyr Glu Pro Glu Ala Tyr Asp Val Pro
        130                 135                 140
Asp Tyr Ala Ser Leu
145

<210> SEQ ID NO 19
<211> LENGTH: 149
<212> TYPE: PRT
<213> ORGANISM: Artificial Sequence
<220> FEATURE:
<223> OTHER INFORMATION: Synthetic

<400> SEQUENCE: 19

Tyr Asp Val Pro Asp Tyr Ala Ser Leu Met Asp Val Phe Met Lys Gly
1               5                   10                  15
Leu Ser Lys Ala Lys Glu Gly Val Val Ala Ala Glu Lys Thr Lys
            20                  25                  30
Gln Gly Val Ala Glu Ala Ala Gly Lys Thr Lys Glu Gly Val Leu Tyr
        35                  40                  45
Val Gly Ser Lys Thr Lys Glu Gly Val Val His Gly Val Ala Thr Val
    50                  55                  60
Ala Glu Lys Thr Lys Glu Gln Val Thr Asn Val Gly Gly Ala Val Val
65                  70                  75                  80
Thr Gly Val Thr Ala Val Ala Gln Lys Thr Val Glu Gly Ala Gly Ser
                85                  90                  95
Ile Ala Ala Ala Thr Gly Phe Val Lys Lys Asp Gln Leu Gly Lys Asn
                100                 105                 110
Glu Glu Gly Ala Pro Gln Glu Gly Ile Leu Glu Asp Met Pro Val Asp
            115                 120                 125
Pro Asp Asn Glu Ala Tyr Glu Met Pro Ser Glu Glu Gly Tyr Gln Asp
        130                 135                 140
Tyr Glu Pro Glu Ala
145

<210> SEQ ID NO 20
<211> LENGTH: 150
<212> TYPE: PRT
<213> ORGANISM: Artificial Sequence
<220> FEATURE:
<223> OTHER INFORMATION: Synthetic

<400> SEQUENCE: 20

Met Asp Val Phe Met Lys Gly Leu Ser Lys Ala Lys Glu Gly Val Val
```

```
            1               5                  10                 15
Ala Ala Ala Glu Lys Thr Lys Gln Gly Val Ala Glu Ala Ala Gly Lys
                    20                  25                  30

Thr Lys Glu Gly Val Leu Tyr Val Gly Ser Lys Thr Lys Glu Gly Val
                35                  40                  45

Val His Gly Val Ala Thr Val Ala Glu Lys Thr Lys Glu Gln Val Thr
            50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
                    85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
                115                 120                 125

Ser Glu Glu Gly Tyr Gln Asp Tyr Glu Pro Glu Ala Glu Gln Lys Leu
                130                 135                 140

Ile Ser Glu Glu Asp Leu
145                 150

<210> SEQ ID NO 21
<211> LENGTH: 150
<212> TYPE: PRT
<213> ORGANISM: Artificial Sequence
<220> FEATURE:
<223> OTHER INFORMATION: Synthetic

<400> SEQUENCE: 21

Glu Gln Lys Leu Ile Ser Glu Glu Asp Leu Met Asp Val Phe Met Lys
1               5                   10                  15

Gly Leu Ser Lys Ala Lys Glu Gly Val Val Ala Ala Ala Glu Lys Thr
                20                  25                  30

Lys Gln Gly Val Ala Glu Ala Ala Gly Lys Thr Lys Glu Gly Val Leu
                35                  40                  45

Tyr Val Gly Ser Lys Thr Lys Glu Gly Val Val His Gly Val Ala Thr
            50                  55                  60

Val Ala Glu Lys Thr Lys Glu Gln Val Thr Asn Val Gly Gly Ala Val
65                  70                  75                  80

Val Thr Gly Val Thr Ala Val Ala Gln Lys Thr Val Glu Gly Ala Gly
                85                  90                  95

Ser Ile Ala Ala Ala Thr Gly Phe Val Lys Lys Asp Gln Leu Gly Lys
                100                 105                 110

Asn Glu Glu Gly Ala Pro Gln Glu Gly Ile Leu Glu Asp Met Pro Val
                115                 120                 125

Asp Pro Asp Asn Glu Ala Tyr Glu Met Pro Ser Glu Glu Gly Tyr Gln
                130                 135                 140

Asp Tyr Glu Pro Glu Ala
145                 150

<210> SEQ ID NO 22
<211> LENGTH: 154
<212> TYPE: PRT
<213> ORGANISM: Artificial Sequence
<220> FEATURE:
<223> OTHER INFORMATION: Synthetic

<400> SEQUENCE: 22
```

```
Met Asp Val Phe Met Lys Gly Leu Ser Lys Ala Lys Glu Gly Val Val
1               5                   10                  15
Ala Ala Ala Glu Lys Thr Lys Gln Gly Val Ala Glu Ala Ala Gly Lys
            20                  25                  30
Thr Lys Glu Gly Val Leu Tyr Val Gly Ser Lys Thr Lys Glu Gly Val
        35                  40                  45
Val His Gly Val Ala Thr Val Ala Glu Lys Thr Lys Glu Gln Val Thr
    50                  55                  60
Asn Val Gly Gly Ala Val Val Thr Gly Val Thr Ala Val Ala Gln Lys
65                  70                  75                  80
Thr Val Glu Gly Ala Gly Ser Ile Ala Ala Ala Thr Gly Phe Val Lys
            85                  90                  95
Lys Asp Gln Leu Gly Lys Asn Glu Glu Gly Ala Pro Gln Glu Gly Ile
                100                 105                 110
Leu Glu Asp Met Pro Val Asp Pro Asp Asn Glu Ala Tyr Glu Met Pro
            115                 120                 125
Ser Glu Glu Gly Tyr Gln Asp Tyr Glu Pro Glu Ala Gly Lys Pro Ile
        130                 135                 140
Pro Asn Pro Leu Leu Gly Leu Asp Ser Thr
145                 150

<210> SEQ ID NO 23
<211> LENGTH: 154
<212> TYPE: PRT
<213> ORGANISM: Artificial Sequence
<220> FEATURE:
<223> OTHER INFORMATION: Synthetic

<400> SEQUENCE: 23

Gly Lys Pro Ile Pro Asn Pro Leu Leu Gly Leu Asp Ser Thr Met Asp
1               5                   10                  15
Val Phe Met Lys Gly Leu Ser Lys Ala Lys Glu Gly Val Val Ala Ala
            20                  25                  30
Ala Glu Lys Thr Lys Gln Gly Val Ala Glu Ala Ala Gly Lys Thr Lys
        35                  40                  45
Glu Gly Val Leu Tyr Val Gly Ser Lys Thr Lys Glu Gly Val Val His
    50                  55                  60
Gly Val Ala Thr Val Ala Glu Lys Thr Lys Glu Gln Val Thr Asn Val
65                  70                  75                  80
Gly Gly Ala Val Val Thr Gly Val Thr Ala Val Ala Gln Lys Thr Val
            85                  90                  95
Glu Gly Ala Gly Ser Ile Ala Ala Ala Thr Gly Phe Val Lys Lys Asp
                100                 105                 110
Gln Leu Gly Lys Asn Glu Glu Gly Ala Pro Gln Glu Gly Ile Leu Glu
            115                 120                 125
Asp Met Pro Val Asp Pro Asp Asn Glu Ala Tyr Glu Met Pro Ser Glu
        130                 135                 140
Glu Gly Tyr Gln Asp Tyr Glu Pro Glu Ala
145                 150
```